(12) United States Patent
Varki et al.

(10) Patent No.: US 8,541,231 B2
(45) Date of Patent: Sep. 24, 2013

(54) ELIMINATION OF N-GLYCOLYLNEURAMINIC ACID FROM ANIMAL PRODUCTS FOR HUMAN USE

(75) Inventors: Ajit Varki, La Jolla, CA (US); Anna Maria Hedlund, San Diego, CA (US); Dzung Nguyen, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/528,507

(22) Filed: Jun. 20, 2012

(65) Prior Publication Data

US 2013/0039991 A1 Feb. 14, 2013

Related U.S. Application Data

(62) Division of application No. 12/600,378, filed as application No. PCT/US2006/022282 on Jun. 8, 2006, now Pat. No. 8,232,448.

(60) Provisional application No. 60/688,867, filed on Jun. 8, 2005.

(51) Int. Cl.
| | | |
|---|---|---|
| *C12N 5/07* | (2010.01) | |
| *C12N 5/10* | (2006.01) | |
| *A01N 63/00* | (2006.01) | |
| *A61K 48/00* | (2006.01) | |

(52) U.S. Cl.
USPC ........................................ 435/354; 424/93.21

(58) Field of Classification Search
USPC ...................................... 435/354; 424/93.21
See application file for complete search history.

(56) References Cited

U.S. PATENT DOCUMENTS 8,232,448 B2 * 7/2012 Varki et al. ...................... 800/18

FOREIGN PATENT DOCUMENTS

WO    WO2005/033303    4/2005

OTHER PUBLICATIONS

Clark et al. Nature Reviews: Genetics. 2003, 825-833.*
Niemann et al (Rev. Sci, Tech. Off. Int. Spiz. 2005, (24), 285-298.*
Wheeler. Theriogenology. 2001, (56), 1345-1369.*
Prelle, Anat. Histol. Embryol. 2002, vol. 31, 169-186.*
Smith. Journal of Biotechnology, 99:1-22, 2002.*
Denning and Priddle. Reproduction, 126:1-11. 2003.*
Mullins et al. Hypertension 22:630-633 (1993).*
Cao et al. J. of Exp. Zoo., 311A: 368-376, 2009.*
Brevini et al. Theriogenology, 74: 544-550, 2010.*
Paris et al. Theriogenology, 74: 516-524, 2010.*
Wright et al. ILAR Journal, 45(3): 314-323, 2004.*
Taniguichi et al. Genome Biology, 7: R116.1-R116.14, 2006.*
Capecchi. Scientific American, 1994, 270:34-41.*
Kawano et al. (JBC, 270(27): 16458-16463, 1995).*
Conner, Current Protocols in Molecular Biology, 23.4.1-23.4.9, 2000.*
Irie et al., (1998) JBC, vol. 273(25), pp. 15866-15871.

* cited by examiner

*Primary Examiner* — Thaian N Ton
(74) *Attorney, Agent, or Firm* — Medlen & Carroll, LLP

(57) ABSTRACT

The application is in the field of transgenic (non-human) organisms, sialic acid chemistry, metabolism and antigenicity. More particularly, the invention is related to a method to produce Neu5Gc-free animals and products therefrom comprising disrupting the CMAH gene and thereby reducing or eliminating Neu5Gc from biological material of non-humans.

2 Claims, 13 Drawing Sheets

ELIMINATION OF N-GLYCOLYLNEURAMINIC ACID FROM ANIMAL PRODUCTS FOR HUMAN USE

This application is a divisional of co-pending application Ser. No. 12/600,378 filed on Nov. 16, 2009, which is the U.S. national Stage Application filed under 35 U.S.C. §371 and claims priority to International Application No. PCT/US06/22282, filed Jun. 8, 2006, now abandoned, which claims the benefit of priority to Provisional Application U.S. Ser. No. 60/688,867, which was filed on Jun. 8, 2005, the disclosures of which are incorporated herein by reference.

GOVERNMENT INTEREST

This invention was made with government support from the National Institutes of Health under grant number R01CA38701.

TECHNICAL FIELD

The application is in the field of transgenic (non-human) organisms, sialic acid chemistry, metabolism and antigenicity.

BACKGROUND

All cells are covered with a dense and complex array of sugar chains. Sialic acids (Sias) are a family of nine-carbon sugars that are typically present at the outermost units of these sugar chains. By virtue of their terminal position, sialic acids act as binding sites for many exogenous and endogenous receptors such as the Influenza viruses and the Siglec family of endogenous proteins. Such sugars are thus useful drug targets for the prevention and treatment of infection. They are also involved in various biological and pathological processes such as neuronal plasticity and cancer metastasis. In many of these instances, the precise structures of the sialic acid and the residues it is attached to play critical roles. Thus, studying sialic acid functions is of great biological importance. In addition, many sialic acids are obtained through certain dietary sources (red meat and diary products), and may also be associated with certain disease states, such as cancer and heart disease.

SUMMARY OF THE INVENTION

The application is in the field of transgenic (non-human) organisms, sialic acid chemistry, metabolism and antigenicity.

The animals contemplated for use in the practice of the invention are those animals generally regarded as useful for the processing of food stuffs, i.e. avian such as meat bred and egg laying chicken and turkey, ovine such as lamb, bovine such as beef cattle and milk cows, piscine and porcine.

In one embodiment, the invention is a method to produce Neu5Gc-free animals and products therefrom comprising disrupting the CMAH gene and thereby reducing or eliminating Neu5Gc from biological material of non-humans. The CMAH gene may be disrupted by frame-shift mutation or the cre-lox system. The biological material can be virtually any non-human organic material suspected of containing Neu5Gc, such as a food sample (for example, red meat or a dairy product) or a clinical sample. The clinical sample may be from any non-human animal source, such as avian, ovine, bovine, piscine and porcine. Non-human clinical samples can be from any body fluid or tissue, such as serum, muscle tissue and milk, etc. The Neu5Gc-free animals may be for consumption by humans, for the purpose of culturing human cells in laboratories and in the biotechnology industry, and for products for use in the cosmetic industry.

In another embodiment, the invention is a transgenic non-human animal comprising Neu5Gc-free serum, muscle tissue and milk. The transgenic animal may be avian, ovine, bovine, piscine and porcine. Additionally, the transgenic animal may be for consumption by humans. The serum may be used to culture human cells in laboratories and in the biotechnology industry, and may be used for products in cosmetics which would reduce the risk of immune responses against such products.

Figure 6:
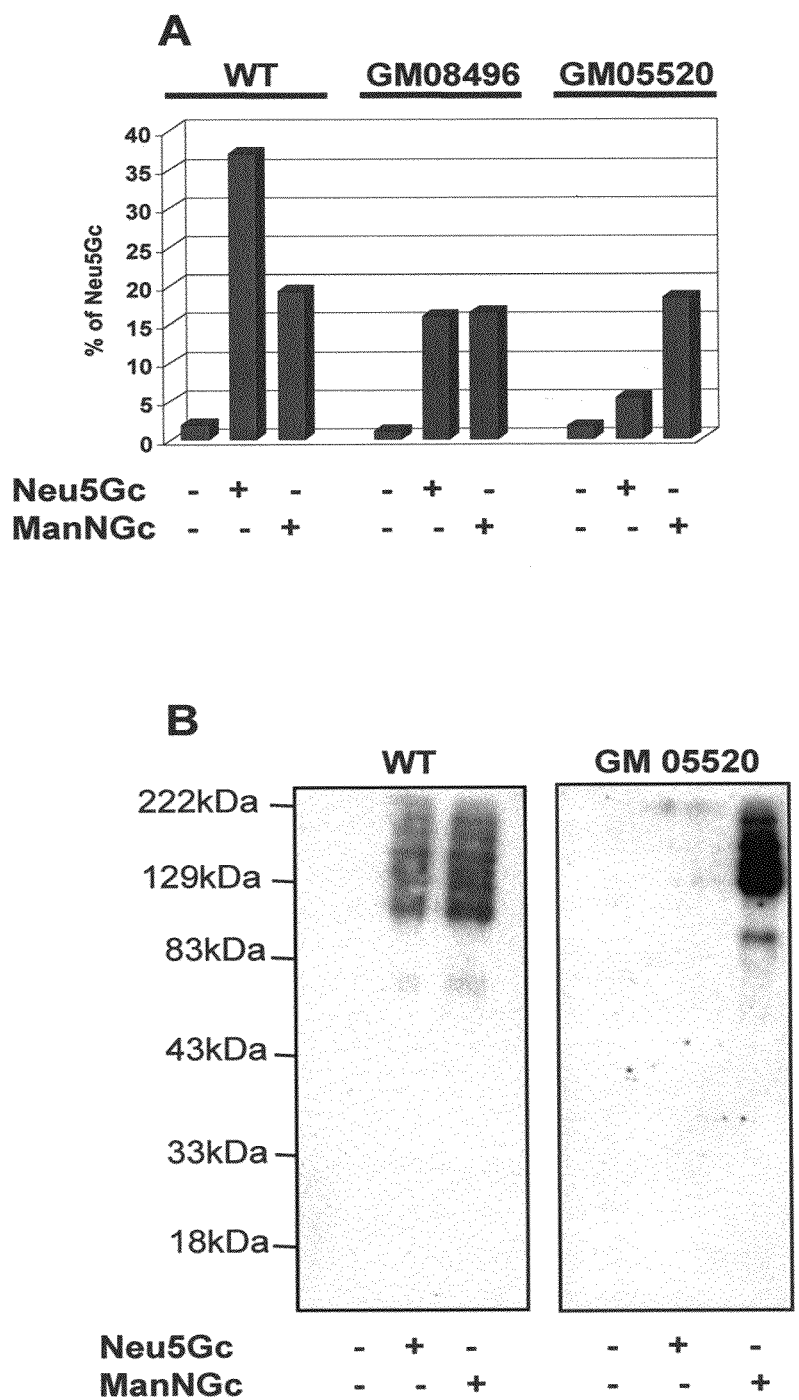

FIG. 6 depicts the lysosomal sialic acid transporter is involved in the metabolic incorporation of free Neu5Gc. Wild-type (WT) and lysosomal Sialic acid transporter mutant human fibroblasts (GM08496 and GM05520) grown in human serum, were fed for 3 days with 3 mM Neu5Gc, ManNGc or Neu5Ac. The cells were then harvested, fractionated and the Sia content in the different fractions analysed by DMB derivatization followed by HPLC. (A) The proportion of Neu5Gc (expressed as percent of total Sia) in the membrane fraction is shown. (B) Western blot analysis of proteins extracted from the membrane fractions of wild-type and GM05520 mutant human fibroblasts, using an anti-Neu5Gc antibody, after Neu5Gc or ManNGc feeding.

Figure 7:
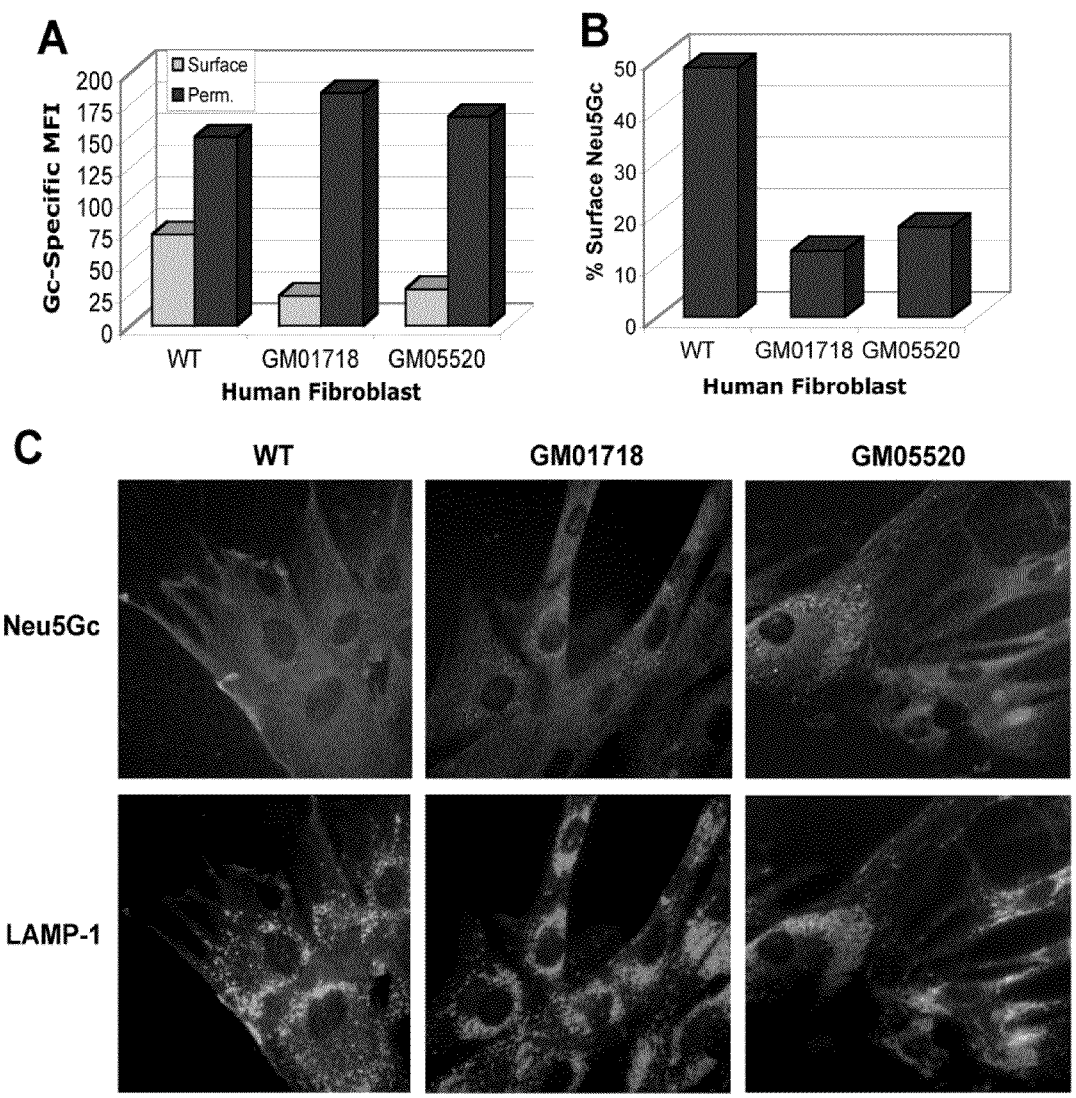

FIG. 7 depicts the lysosomal sialidase and sialic acid transporter are required for metabolic incorporation of Neu5Gc from serum glycoconjugates. WT fibroblasts, lysosomal sialidase mutant fibroblasts (GM01718) and Sia transporter mutant fibroblasts (GM05520) were incubated with 10% FCS plus 20% horse serum (rich sources of glycosidically-bound Neu5Gc) for 3 days. (A) Cells were then released from the flasks, fixed and analyzed for binding of a chicken anti-Neu5Gc antibody, with and without permeabilization by flow cytometry. Neu5Gc-specific MFI is the median fluorescence intensity (MFI) of the chicken anti-Neu5Gc staining with the background secondary alone MFI subtracted out. At least 5000 cells were counted for each staining. (B) Percent surface Neu5Gc was calculated by dividing the non-permeabilized Neu5Gc-specific MFI by the permeabilized Neu5Gc-specific MFI, (C) WT, GM01718, and GM05520 fibroblasts were grown on slides for 4 days, fixed, permeabilized and stained with chicken anti-Neu5Gc IgY and mouse anti-LAMP-1 IgG1. Antibody binding was detected with FITC-goat anti-chicken IgY and Cascade Blue-goat anti-mouse IgG.

Figure 8:
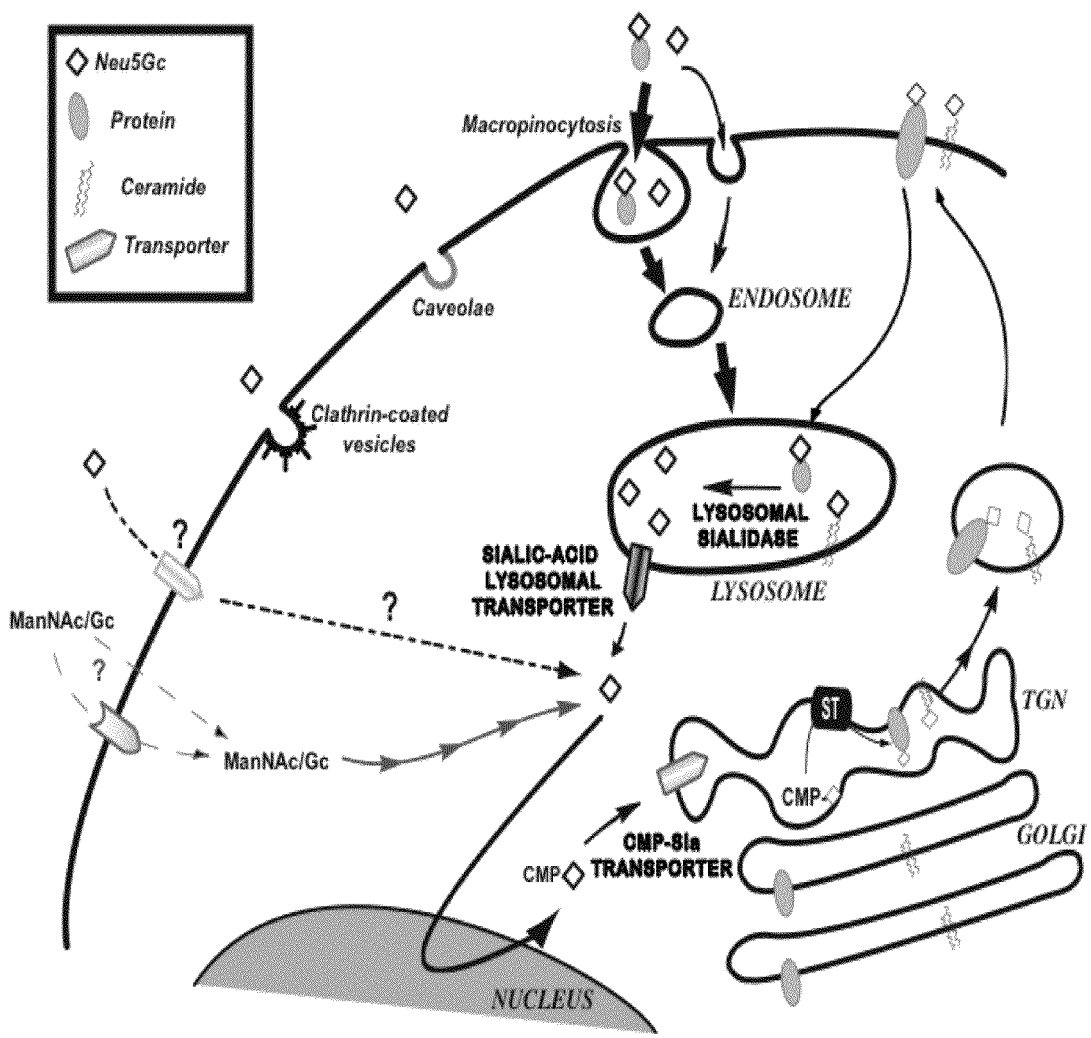

FIG. 8 depicts proposed pathways for the uptake and incorporation of Neu5Gc in human cells. The model proposed is based on the data presented in this study and upon prior literature. The diamond shape represents a Neu5Gc molecule. The thickness of the various arrows suggests the relative importance of various pathways in delivering Neu5Gc into the cell.

Figure 9:
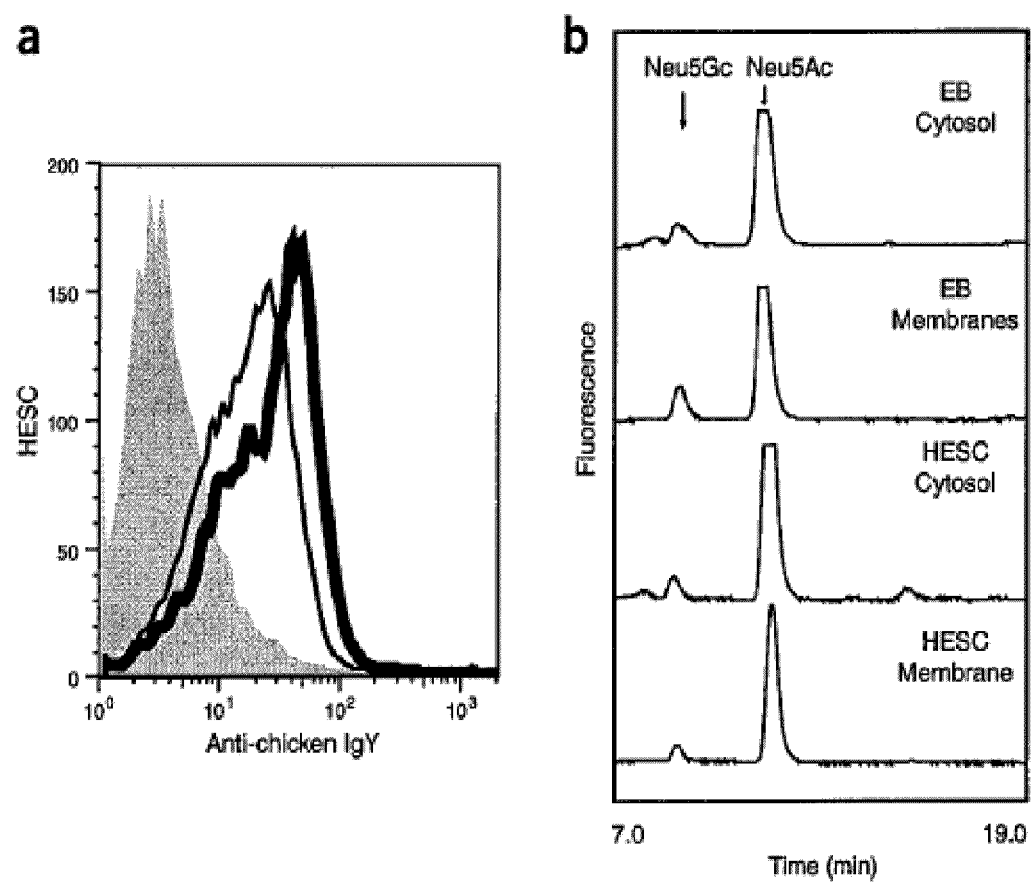

FIGS. 9a-b depict detection of Neu5Gc on Human embryonic stem cells (HESC) Cultured under Conventional Conditions. EGFP transfected HESC were grown under conventional conditions using a murine feeder layer and medium containing 20% "KNOCKOUT" serum replacement. a. HESC were released with 2 mM EDTA and studied by flow cytometry using a previously described affinity-purified polyclonal monospecific antibody against Neu5Gc followed by a secondary Cy5-conjugated anti-chicken IgY antibody. Gray shaded plot: secondary antibody only; thick line: primary and secondary antibody; thin line: cells incubated with chicken anti-Neu5Gc in the presence of 1% chimp serum that contains Neu5Gc. b. HESC were isolated by FACS sorting using the intrinsic EGFP fluorescence. Embryoid bodies were derived by removing the feeder layer and growing the HESC in reduced serum medium for 5 days. Both types of cells were fractionated into membrane and cytosolic components. Sias were released and analyzed by DMB derivatization and HPLC. A peak corresponding to Neu5Gc is seen in all fractions.

Figure 10:
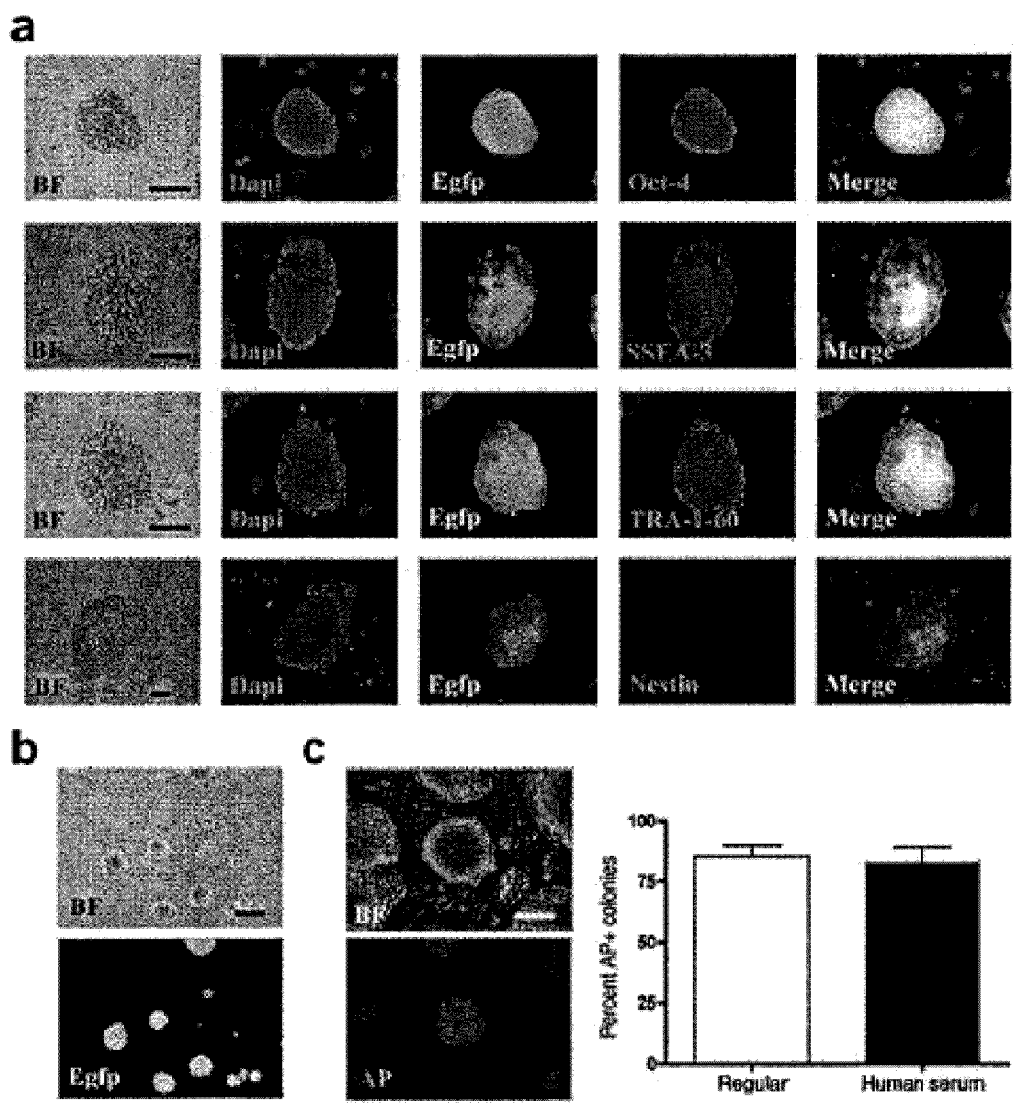

FIGS. 10a-c depict HESC stably expressing EGFP can remain undifferentiated when NHS is substituted for animal-derived culture medium components. a. Bright Field Images (BF) of undifferentiated HESC, scale bars correspond to 100 µm. HESC are positive for EGFP and for several non-differentiation markers, such as Oct-4, SSEA-3, and TRA-1-60. Staining for nestin, a neural progenitor marker, was negative, indicating the HESC are not differentiated. b. Bright field image of EB-derived from EGFP-expressing HESC. They maintain the EGFP expression after differentiation. c. HESC colonies were positive for alkaline phosphatase (AP) activity, as shown in the fluorescent image, both with the standard serum replacement (regular) and in human serum. Cells were also negative for SSEA-1 and for neural markers such as Nestin, Tuj-1, Map2(a+b), NeuN, astrocyte markers GFAP and S100-β; and oligodendrocyte markers 04, GSM and RIP (data not shown).

Figure 11:
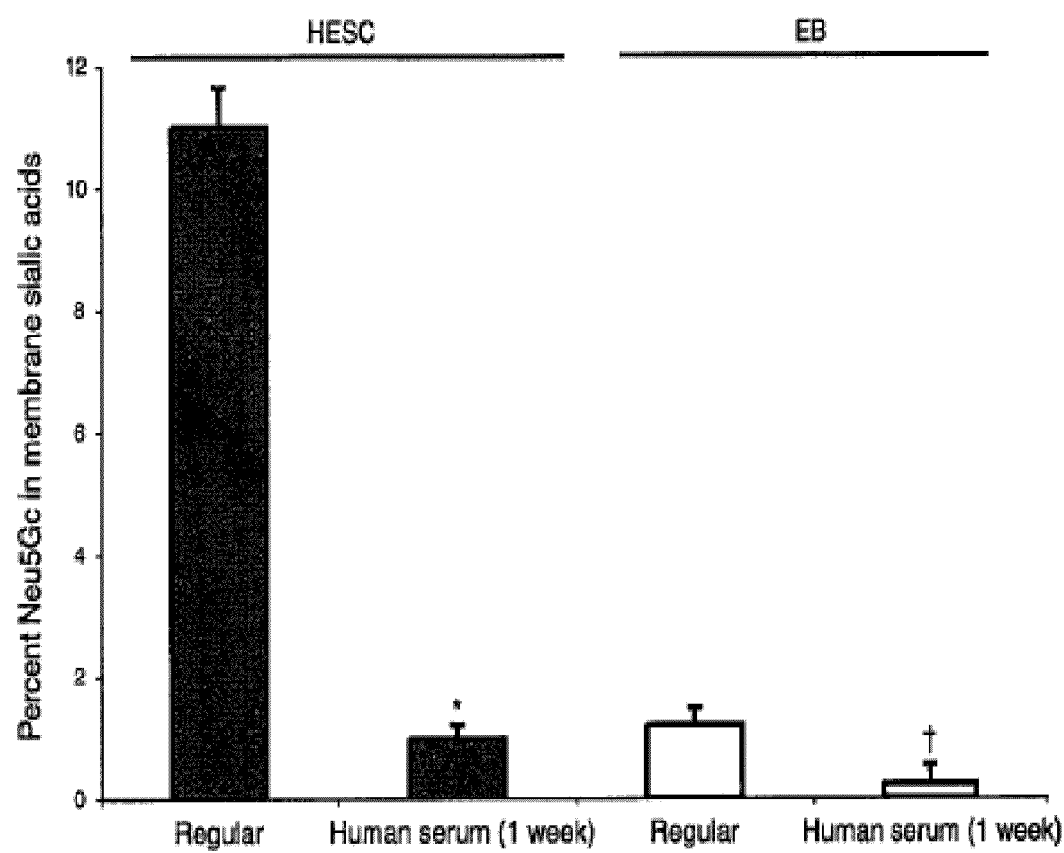

FIG. 11 depicts effect of growth in NHS on Neu5Gc content of HESC and Embryoid Bodies. HESC or embryoid bodies were grown in NHS instead of the standard serum replacement. Membrane-bound Sias were studied for percentage of Neu5Gc as described in the legend to FIG. 1b. Data represent the mean of two different experiments (mean±SD). *: $p<0.005$, †: $p<0.01$.

Figure 3:
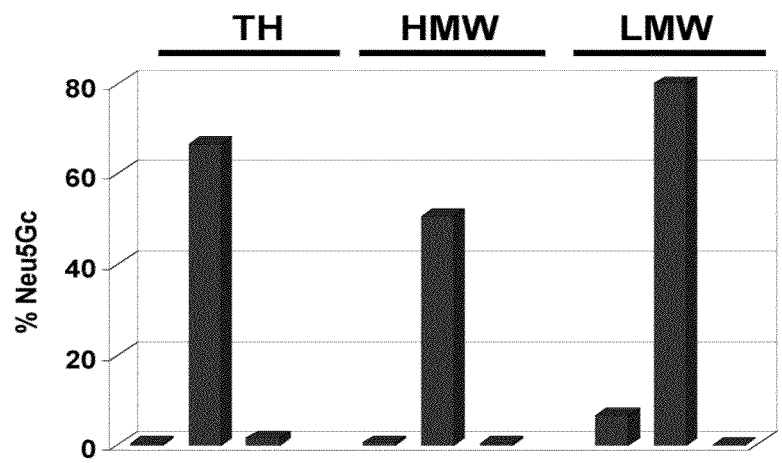
FIG. 3 depicts uptake of free Neu5Gc not specific for human cells. Human and Chimpanzee EBV-transformed lymphoblasts were fed or not, for 3 days with 3 mM Neu5Gc or Neu5Ac, and the cells were then harvested, fractionated and the Sia content in the different fractions analysed by DMB derivatization followed by HPLC. The proportion of Neu5Gc (expressed as percent of total Sia) of the different fractions from (A) human lymphoblasts and (B) Chimpanzee lymphoblasts is shown. TH: Total homogenate; HMW: High Molecular Weight fraction, LMW: Cytosolic LMW fraction.
Figure 3:
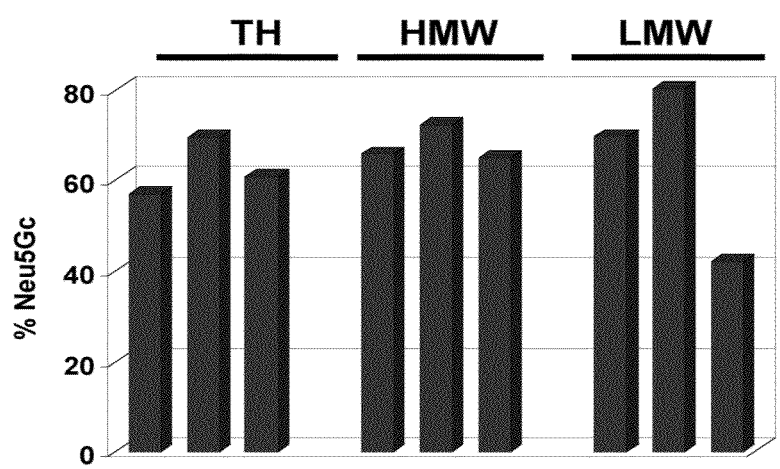
Figure 5:
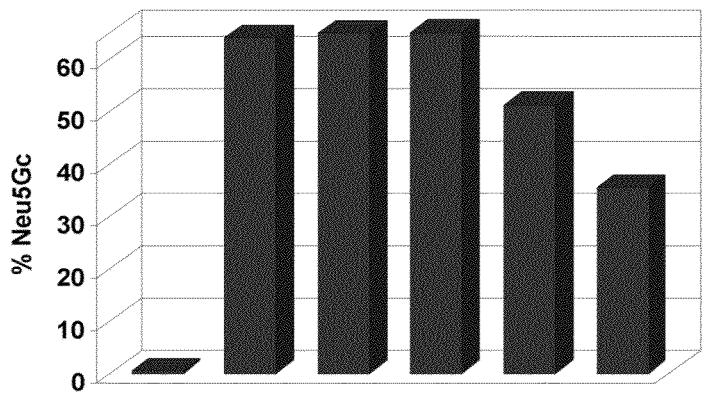
FIG. 5 depicts free Neu5Gc entering cells via endocytic processes. Caco-2 cells grown in human serum were fed for 3 days with 3 mM Neu5Gc in the presence or absence of various inhibitors of endocytic pathways. The cells were then harvested, fractionated and the Sia content in the different fractions analysed by DMB derivatization followed by HPLC. The proportion of Neu5Gc (as percent of total Sia) of (A) total homogenate fraction and (B) membrane fraction is shown.
Figure 5:
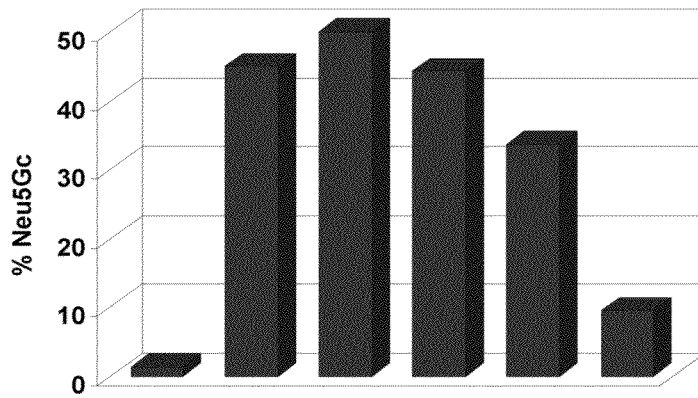
Figure 12:
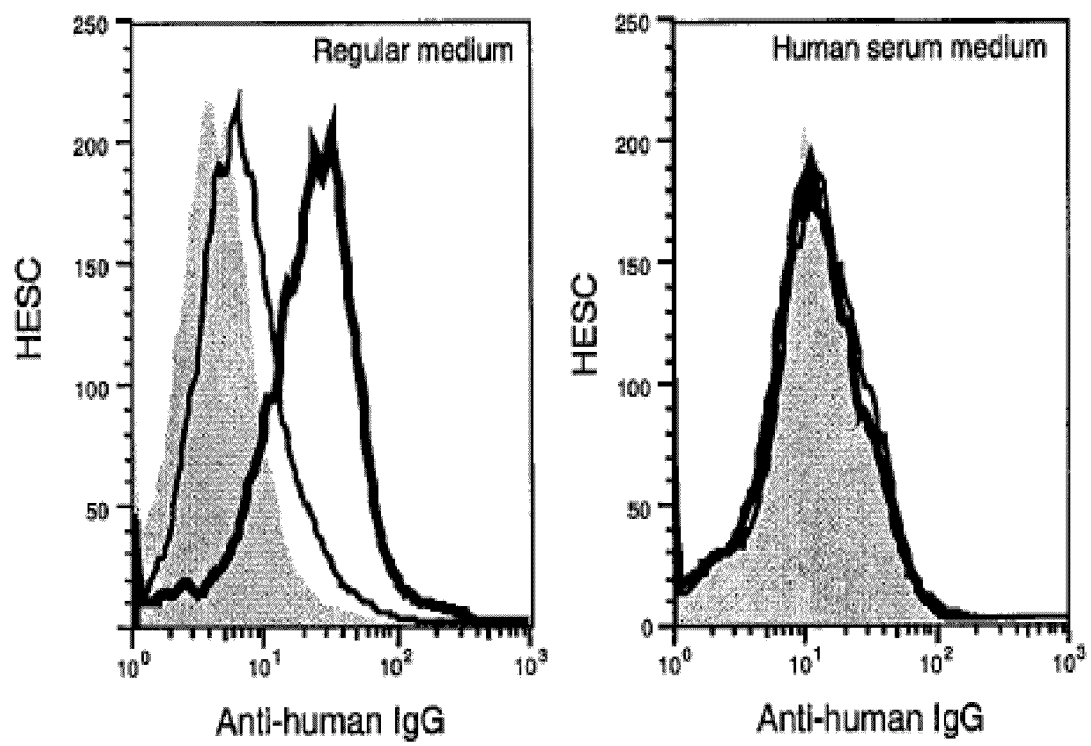

FIG. 12 depicts binding of "Natural" Antibodies from Sera of Normal Human Donors to HESC. HESC were grown in regular medium or in NHS as in FIG. 3 for 5 days. The cells were released with 2 mM EDTA and then exposed to a normal serum from a human with a high level of anti-Neu5Gc antibodies (thick line) or from another individual with a low level of such antibodies (thin line) for 55 min, then stained with a secondary goat anti-human IgG conjugated to Alexa 594, and studied by flow cytometry, with gating on the EGFP-positive HESC. The gray shaded plot shows the result with secondary antibody alone. Ig deposition was markedly reduced when cells were first grown in NHS-containing medium for 5 days (although non-specific background levels were increased, see lower panel). The somewhat higher background seen when HESC were grown in NHS-containing medium could be due to a non-specific IgG absorption, but it had no major consequences, such as complement deposition (see FIG. 5).

Figure 13:
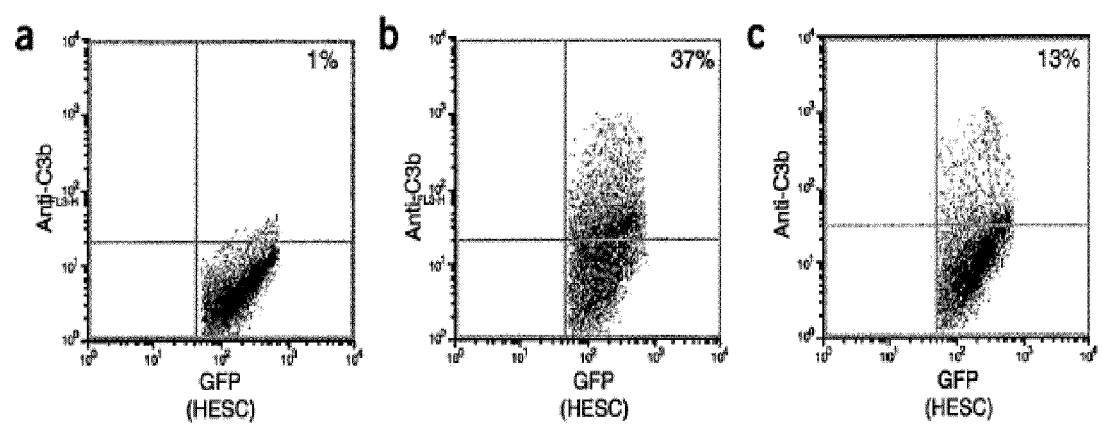

FIG. 13 depicts binding of Complement C3b from Human Sera to HESC. HESC were grown in regular medium or in NHS-containing medium for 5 days and harvested with 2 mM EDTA as in FIG. 3. The cells were then exposed to a normal human serum from an individual with a high level of anti-Neu5Gc antibodies for 15 min at 37° C., and also to the serum from an individual with a low level of anti-Neu5Gc antibodies. Deposited C3b was detected using a goat anti-human C3, then stained with a goat anti-human C3b conjugated to Alexa 594 and studied by flow cytometry. Control cells that were not exposed to the any human sera showed no positive staining for C3b (panel a). After exposure to the high level of anti-Neu5Gc antibodies serum, the double fluorescence plot shows that 37% of the EGFP+ cells HESC grown in regular medium showed positive staining for human C3b (panel c), whereas only 13% of the EGFP+ cells grown in human serum-containing medium were positive for C3b (panel d). In the case of the cells that were exposed to the low level of anti-Neu5Gc antibodies serum, only 22% of the EGFP+ cells were positive for human C3b (panel b, note that the levels were much lower since the Y axis is on a log scale).

DETAILED DESCRIPTION

The application is in the field of transgenic (non-human) organisms, sialic acid chemistry, metabolism and antigenicity.

Sialic acids are nine-carbon sugars found on the surface of most mammalian cells. The two most common forms of sialic acids are N-acetylneuraminic acid (Neu5Ac) and N-glycolylneuraminic acid (Neu5Gc), which differ by only one oxygen atom. Unlike all other mammals, humans are unable to synthesize Neu5Gc due to a mutation in the CMP-Neu5Ac hydroxylase (CMAH) gene, which converts Neu5Ac to Neu5Gc. Despite the lack of CMAH in genes, small amounts of Neu5Gc have been found in healthy human tissues as well as malignant tissues. Research has shown that the incorporated Neu5Gc may originate from dietary sources (Tangvoranuntakul et al., 2003). Red meat like beef, pork and lamb are particularly rich in Neu5Gc and should be considered the primary source of Neu5Gc in human diet. Also dairy products contain Neu5Gc although at somewhat lower levels than in red meat. Considering that most humans also have antibodies to Neu5Gc, incorporation of Neu5Gc is hypothesized to be one of the factors contributing to the health risks associated with high consumption of red meat (heart disease, certain types of cancers). The presence of Neu5Gc in animal products is also a potential source of allergenicity. Additionally, when human cells are cultured in serum from animals they can take up and incorporate Neu5Gc, potentially resulting in immunological rejection if such cells are used for therapy (e.g. transplantation of human embryonic stem cell-derived grafts). It has now been demonstrated that targeted disruption of the CMAH gene in mice completely abolished the expression of Neu5Gc in all tissues as well as in their secretions. Similar disruption of the CMAH gene in domesticated livestock (cows, pigs, goats etc.) may provide a source of Neu5Gc-free meat, milk, and other food products, items used in research, e.g. serum, as well as in cosmetics.

By targeting one single gene, CMAH, Neu5Gc can be eliminated from all mouse tissues and secretions, including serum, muscle tissue and milk. Since Neu5Gc is immunogenic to humans, eliminating CMAH from domesticated animals would provide a source of Neu5Gc products for human use and consumption. For example, a CMAH null cows would avoid uptake and incorporation of Neu5Gc from ingested meat, milk etc. This is a unique intervention, which would provide humans with a safer source of bovine food items and other products, and hence reducing the risk of developing potentially autoreactive antibodies. The absence of Neu5Gc in bovine serum products used for human cell tissue culture would also provide more human-like growth conditions.

The same methodology as was used to knock out CMAH in mice, would be employed to disrupt CMAH gene expression in domesticated animals. For mice, a frame-shift mutation, similar to the one found in the human CMAH, was introduced using the Cre-Lox recombination system. While normal wild-type mice express equal levels of Neu5Gc and Neu5Ac in their muscle tissue, and approximately 5% Neu5Gc in their milk, we found no evidence for Neu5Gc expression in tissues or milk of the CMAH null mice. Since the mice are otherwise viable and fertile (as are humans), we can predict that other CMAH nulls animals will also be the same.

The use of Neu5Gc-free products could be applicable to several commercial settings. First, if consumption of Neu5Gc indeed turns out to be a significant risk to human health, meat from Neu5Gc-free animals would provide a safer alternative source of red meat. Secondly, this could replace normal animal serum which are currently used to culture human cells in laboratories, and in the biotechnology industry. Thirdly, the use of Neu5Gc-free bovine products in cosmetics would reduce the risk of immune responses against such products.

N-glycolylneuraminic acid (Neu5Gc) is a widely expressed sialic acid in mammalian cells. While humans are genetically deficient in producing Neu5Gc, small amounts are present in human cells in vivo. A dietary origin was suggested by human volunteer studies, and by observing that free Neu5Gc is metabolically incorporated into cultured human carcinoma cells, by unknown mechanisms. We now show that free Neu5Gc uptake also occurs in other human and mammalian cells. Inhibitors of certain non-clathrin mediated endocytic pathways reduce Neu5Gc accumulation. Studies with human mutant cells show that the lysosomal sialic acid transporter is required for metabolic incorporation of free Neu5Gc. Incorporation of glycosidically-bound Neu5Gc from exogenous glycoconjugates (relevant to human gut epithelial exposure to dietary Neu5Gc) requires the transporter, as well as the lysosomal sialidase, which presumably acts to release free Neu5Gc. Thus, exogenous Neu5Gc reaches lysosomes via pinocytic/endocytic pathways, and is exported in free form into the cytosol, becoming available for activation and transfer to glycoconjugates. In contrast, N-glycolylmannosamine (ManNGc) apparently traverses the plasma membrane by passive diffusion and becomes available for conversion to Neu5Gc in the cytosol. This mechanism can also explain the metabolic incorporation of chemically synthesized unnatural sialic acids, as reported by others. Finally, it is believed that this is the first example of delivery to the cytosol of an extracellular small molecule that cannot cross the plasma membrane—utilizing fluid pinocytosis and a specific lysosomal transporter. The approach could thus potentially be generalized to any small molecule that has a specific lysosomal transporter, but not a plasma membrane transporter.

Sialic acid (Sia) is a generic name for a family of acidic nine carbon sugars typically found as the outermost units of glycan chains on the vertebrate cellular glycocalyx and on secreted glycoproteins. Their location and widespread occurrence on all vertebrate cells allow them to be involved in processes such as pathogen binding, inflammation, immune response and tumor metastasis.

There are more than 50 kinds of Sias known in nature. Most are derived via biosynthetic modification of a Sia called N-acetylneuraminic acid (Neu5Ac). The addition of a single oxygen atom to the N-acetyl group of Neu5Ac gives a very common variation called N-glycolylneuraminic acid (Neu5Gc). The surfaces of most primate cell types studied to date are dominated by two major Sias, which are Neu5Ac and Neu5Gc.

Sialic acids (Sias) are a family of acidic sugars displayed on the surfaces of all cell types, and on many secreted proteins. The two most common mammalian Sias are N-glycolylneuraminic acid (Neu5Gc) and N-acetylneuraminic acid (Neu5Ac), with Neu5Ac being the metabolic precursor of Neu5Gc. Humans are genetically unable to produce Neu5Gc from Neu5Ac, due to a mutation that occurred after our common ancestor with great apes. Thus, while human cells have no overall loss of Sias, they express primarily Neu5Ac. However, they can potentially take Neu5Gc up from media containing animal products, activate it into CMP-Neu5Gc, and metabolically incorporate it using the same Golgi transporter and sialyltransferases as CMP-Neu5Ac. Most normal healthy humans have circulating anti-Neu5Gc antibodies. Thus, xenogenic culture methodology could compromise transplantation success, due to uptake and expression of Neu5Gc on the surface of any tissue developed from HESC. Such incorporation could induce an immune response upon transplantation.

In order for a Sia molecule to get attached to glycoconjugates, it must first be activated by conversion to the sugar nucleotide derivative cytidine-monophosphate-Sia (CMP-Sia). Thus, Sias are converted to CMP-Sias in the nucleus, which then return to the cytosol in order to be transported into the Golgi apparatus, where they serve as high-energy donors for attaching Sias to newly synthesized glycoconjugates on their way to the cell surface. The biosynthetic transformation of Neu5Ac to Neu5Gc occurs at this sugar nucleotide level, wherein the CMP-Neu5Ac hydroxylase (CMAH) catalyzes the transfer of an oxygen atom to CMP-Neu5Ac, generating CMP-Neu5Gc. CMP-Neu5Gc can then be transported into the Golgi apparatus and used, in the same manner as CMP-Neu5Ac, to add Neu5Gc to newly synthesized glycoconjugates. Indeed, these two nucleotide sugars appear to be used interchangeably by the Golgi CMP-Sia transporter and by the mammalian sialyltransferases, which transfer Sia residues to cell surface and secreted glycoconjugates. Neu5Ac or Neu5Gc molecules that are released from glycoconjugates during lysosomal degradation processes can also be exported back into the cytosolic compartment by a specific transporter. There, they are both available as substrates for conversion to their respective CMP-Sia forms. Again, there appears to be no major difference in their conversion by CMP-Sia Synthases. In this manner, Neu5Gc can be "recycled" for repeated use in Golgi sialylation reactions.

Although Neu5Gc is a major Sia in most mammalian cells, it was long thought to be absent from healthy human tissues. Indeed, humans are genetically unable to synthesize Neu5Gc, due to an exon deletion/frame shift mutation in the human CMAH gene. It has been estimated that this mutation occurred in the hominid lineage ~2.5 to 3 million years ago. One dramatic consequence of this human-specific genetic defect appears to have been the sudden unmasking of the CD33-related Siglecs during human evolution, since the ancestral condition of these molecules was to recognize Neu5Gc.

Despite the absence of any known alternative pathway for the synthesis of Neu5Gc in humans, various groups have used antibodies to claim the expression of Neu5Gc in human tumors, particularly in various carcinomas. Recent studies from our laboratory re-explored this issue, confirming prior reports of Neu5Gc expression in human cancers and extending the finding to normal human tissues, detecting small amounts of Neu5Gc in epithelial and endothelial cells of normal humans. Definitive confirmation resulted from releasing and purifying sialic acids from such tissues, and identifying a fluorescent derivatized form of Neu5Gc by HPLC and mass spectrometry analysis. Moreover, it was shown that exogenously added free Neu5Gc could be incorporated into cultured human carcinoma cells in vitro. In addition, oral ingestion studies of Neu5Gc in human volunteers were carried out, providing evidence that the Neu5Gc found in human tissues could be originating from dietary sources, particularly red meat and milk products. It now becomes critical to understand the pathway(s) for uptake and metabolic incorporation of Neu5Gc and its potential precursor, N-glycolylmannosamine (ManNGc) into human cells.

HESC can potentially generate every body cell type, making them excellent candidates for cell and tissue replacement therapies. HESC are typically cultured with animal-derived "serum replacements" on murine feeder layers. Both these are sources of the non-human sialic acid Neu5Gc, against which many humans have circulating antibodies. Both HESC and derived embryoid bodies metabolically incorporate significant amounts of Neu5Gc under standard conditions. Exposure to human sera with anti-Neu5Gc antibodies resulted in binding of immunoglobulin and deposition of complement, which would lead to cell killing in vivo. Levels of Neu5Gc on HESC and embryoid bodies dropped after culture in heat-inactivated anti-Neu5Gc-antibody-negative human serum, reducing binding of antibodies and complement from high titer sera, while allowing maintenance of the undifferentiated state. Complete elimination of Neu5Gc would likely require using human serum with human feeder layers, ideally starting with fresh HESC that have never been exposed to animal products.

The pluripotent abilities of human embryonic stem cells (HESC) have potential for treating many diseases by transplantation of HESC-derived tissues. While safety is a major issue regarding infection or tumorigenicity, the possibility of rejection is also of concern. Current culture methods use animal products, carrying the risk of infection by non-human pathogens. HESC lines are traditionally cultured on mitotically-inactivated mouse embryonic fibroblasts (so-called "feeder layers"), and in a media containing fetal calf serum. To avoid animal serum, certain proprietary serum replacements are in use. However, these also contain animal products. When HESC are removed from the feeder layer and grown in suspension, they differentiate into aggregates called embryoid bodies (EB). EB are formed by precursors of several cell lineages and can be induced to differentiate into many cell types. Although the feeder layer is no longer necessary, EB must still be maintained in "serum replacement" medium.

The invention provides knockout non-human organisms lacking a functional CMAH. "Knock-out" refers to partial or complete suppression of the expression of a protein encoded by an endogenous DNA sequence in a cell. The "knock-out" can be affected by targeted deletion of the whole or part of a gene encoding a protein in an embryonic stem cell. As a result, the deletion may prevent or reduce the expression of the protein in any cell in the whole animal in which it is normally expressed. For example, an "CMAH knock-out animal" refers to an animal in which the expression CMAH has been reduced or suppressed by the introduction of a recombinant nucleic acid molecule that disrupts at least a portion of the genomic DNA sequence encoding CMAH.

"Transgenic animal" refers to an animal to which exogenous DNA has been introduced while the animal is still in its embryonic stage. In most cases, the transgenic approach aims at specific modifications of the genome, e.g., by introducing whole transcriptional units into the genome, or by up- or down-regulating pre-existing cellular genes. The targeted character of certain of these procedures sets transgenic technologies apart from experimental methods in which random mutations are conferred to the germline, such as administration of chemical mutagens or treatment with ionizing solution.

The term "knockout mammal" and the like, refers to a transgenic mammal wherein a given gene has been suppressed by recombination with a targeting vector. It is to be emphasized that the term is intended to include all progeny generations. Thus, the founder animal and all F1, F2, F3, and so on, progeny thereof are included.

The term "chimera," "mosaic," "chimeric mammal" and the like, refers to a transgenic mammal with a knockout in some of its genome-containing cells.

The term "heterozygote," "heterozygotic mammal" and the like, refers to a transgenic mammal with a disruption on one of a chromosome pair in all of its genome-containing cells.

The term "homozygote," "homozygotic mammal" and the like, refers to a transgenic mammal with a disruption on both members of a chromosome pair in all of its genome-containing cells.

A "non-human animal" of the invention includes mammals such as rodents, non-human primates, sheep, dog, amphibians, reptiles, avian such as meat bred and egg laying chicken and turkey, ovine such as lamb, bovine such as beef cattle and milk cows, piscine and porcine.

Although the invention uses a typical non-human rodent animal (e.g., including rat and mouse) other animals can similarly be genetically modified using the methods and compositions of the invention.

A "mutation" is a detectable change in the genetic material in the animal, which is transmitted to the animal's progeny. A mutation is usually a change in one or more deoxyribonucleotides, the modification being obtained by, for example, adding, deleting, inverting, or substituting nucleotides.

Typically, the genome of the transgenic non-human animal comprises one or more deletions in one or more exons of the genes and further comprises a heterologous selectable marker gene.

In principle, knockout animals may have one or both copies of the gene sequence of interest disrupted. In the latter case, in which a homozygous disruption is present, the mutation is termed a "null" mutation. In the case where only one copy of the nucleic acid sequence of interest is disrupted, the knockout animal is termed a "heterozygous knockout animal". The knockout animals of the invention are typically homozygous for the disruption of both CMAH genes being targeted.

It is important to note that it is not necessary to disrupt a gene to generate a transgenic organism lacking functional expression. The invention includes the use of antisense molecules that are transformed into a cell, such that production of an OAT polypeptide is inhibited. Such an antisense molecule is incorporated into a germ cell as described more fully herein operably linked to a promoter such that the antisense construct is expressed in all cells of a transgenic organism.

Techniques for obtaining the transgenic animals of the invention are well known in the art; the techniques for introducing foreign DNA sequences into the mammalian germ line were originally developed in mice. One route of introducing foreign DNA into a germ line entails the direct microinjection of linear DNA molecules into a pronucleus of a fertilized one-cell egg. Microinjected eggs are subsequently transferred into the oviducts of pseudopregnant foster mothers and allowed to develop. About 25% of the progeny mice inherit one or more copies of the micro-injected DNA. Currently, the most frequently used techniques for generating chimeric and transgenic animals are based on genetically altered embryonic stem cells or embryonic germ cells. Techniques suitable for obtaining transgenic animals have been amply described. A suitable technique for obtaining completely ES cell derived transgenic non-human animals is described in WO 98/06834.

Knockout animals of the invention can be obtained by standard gene targeting methods as described above, typically by using ES cells. Thus, the invention relates to a method for producing a knockout non-human mammal comprising (i) providing an embryonic stem (ES) cell from the relevant animal species comprising a first intact CMAH gene; (ii) providing a targeting vector capable of disrupting the intact CMAH gene; (iii) introducing the targeting vector into the ES cells under conditions where the intact CMAH undergoes homologous recombination with the targeting vector to produce a mutant CMAH gene; (iv) introducing the ES cells carrying a disrupted CMAH gene into a blastocyst; (v) implanting the blastocyst into the uterus of pseudopregnant female; (vi) delivering animals from said females, identifying a mutant animal that carries the mutant allele and (vii) selecting for knockout animals and breeding them.

A "targeting vector" is a vector comprising sequences that can be inserted into the gene to be disrupted, e.g., by homologous recombination. The targeting vector generally has a 5' flanking region and a 3' flanking region homologous to segments of the gene of interest, surrounding a foreign DNA sequence to be inserted into the gene. For example, the foreign DNA sequence may encode a selectable marker, such as an antibiotics resistance gene. Examples for suitable selectable markers are the neomycin resistance gene (NEO) and the hygromycin β-phosphotransferase gene. The 5' flanking region and the 3' flanking region are homologous to regions within the gene surrounding the portion of the gene to be replaced with the unrelated DNA sequence. DNA comprising the targeting vector and the native gene of interest are contacted under conditions that favor homologous recombination. For example, the targeting vector and native gene sequence of interest can be used to transform embryonic stem (ES) cells, in which they can subsequently undergo homologous recombination.

Thus, a targeting vector refers to a nucleic acid that can be used to decrease or suppress expression of a protein encoded by endogenous DNA sequences in a cell. In a simple example, the knockout construct is comprised of a CMAH polynucleotide with a deletion in a critical portion of the polynucleotide so that a functional CMAH cannot be expressed therefrom. Alternatively, a number of termination codons can be added to the native polynucleotide to cause early termination of the protein or an intron junction can be inactivated. In a typical knockout construct, some portion of the polynucleotide is replaced with a selectable marker (such as the neo gene) so that the polynucleotide can be represented as follows: CMAH 5'/neo/CMAH 3', where CMAH 5' and CMAH 3', refer to genomic or cDNA sequences which are, respectively, upstream and downstream relative to a portion of the CMAH polynucleotide and where neo refers to a neomycin resistance gene.

Proper homologous recombination can be confirmed by Southern blot analysis of restriction endonuclease digested DNA using, as a probe, a non-disrupted region of the gene. Since the native gene will exhibit a restriction pattern different from that of the disrupted gene, the presence of a disrupted gene can be determined from the size of the restriction fragments that hybridize to the probe.

In an animal obtained by the methods above, the extent of the contribution of the ES cells that contain the disrupted CMAH gene to the somatic tissues of the transgenic animal can be determined visually by choosing animal strains for the source of the ES cells and blastocyst that have different coat colors.

In a one embodiment, the knockout animals of the invention are mice. In other embodiments of this invention, the animals are rodents, guinea pigs, rabbits, non-human primates, sheep, dog, cow, amphibians, reptiles, avian such as meat bred and egg laying chicken and turkey, ovine such as lamb, bovine such as beef cattle and milk cows, piscine and porcine. The production of knockout animals is described in further detail below.

The invention further provides for transgenic animals, which can be used for a variety of purposes, e.g., to identify therapeutics agents for CMAH mediated disorders as well as providing sources of food and food products that lack Neu5Gc.

The transgenic animals can typically contain a transgene, such as reporter gene, under the control of an CMAH promoter or fragment thereof. Methods for obtaining transgenic and knockout non-human animals are known in the art. Knock out mice are generated by homologous integration of a "targeting vector" construct into a mouse embryonic stem cell chromosome which encodes a gene to be knocked out. In one embodiment, gene targeting, which is a method of using homologous recombination to modify an animal's genome, can be used to introduce changes into cultured embryonic stem cells. By targeting an CMAH gene of interest in ES cells, these changes can be introduced into the germlines of animals to generate chimeras. The gene targeting procedure is accomplished by introducing into tissue culture cells a DNA targeting vector that includes a segment homologous to a target CMAH locus, and which also includes an intended sequence modification to the CMAH genomic sequence (e.g., insertion, deletion, point mutation). The treated cells are then screened for accurate targeting to identify and isolate those which have been properly targeted.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) J. Embryol. Exp. Mol. Biol. 87:27-45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934). Still another ES cell line is the WW6 cell line (Joffe et al. (1995) PNAS 92;7357-7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) Current Topics in Devel. Biol. 20:357-371); and by Hogan et al. (Manipulating the Mouse Embryo: A Laboratory Manual, Cold Spring Harbor Laboratory Press, Cold Spring Harbor, N.Y. (1986)).

A targeting vector construct refers to a uniquely configured fragment of nucleic acid which is introduced into a stem cell line and allowed to recombine with the genome at the chromosomal locus of the gene of interest to be mutated. Thus a given knock out construct is specific for a given gene to be targeted for disruption. Nonetheless, many common elements exist among these constructs and these elements are well known in the art. A typical targeting vector contains nucleic acid fragments of not less than about 0.5 kb nor more than about 10.0 kb from both the 5' and the 3' ends of the genomic locus which encodes the gene to be mutated. These two fragments are separated by an intervening fragment of nucleic acid which encodes a positive selectable marker, such as the neomycin resistance gene (nee). The resulting nucleic acid fragment, consisting of a nucleic acid from the extreme 5' end of the genomic locus linked to a nucleic acid encoding a positive selectable marker which is in turn linked to a nucleic acid from the extreme 3' end of the genomic locus of interest, omits most of the coding sequence for CMAH or other gene of interest to be knocked out. When the resulting construct recombines homologously with the chromosome at this locus, it results in the loss of the omitted coding sequence, otherwise known as the structural gene, from the genomic locus. A stem cell in which such a homologous recombination event has taken place can be selected for by virtue of the stable integration into the genome of the nucleic acid of the gene encoding the positive selectable marker and subsequent selection for cells expressing this marker gene in the presence of an appropriate drug (neomycin in this example).

Variations on this basic technique also exist and are well known in the art. For example, a "knock-in" construct refers to the same basic arrangement of a nucleic acid encoding a 5' genomic locus fragment linked to nucleic acid encoding a positive selectable marker which in turn is linked to a nucleic acid encoding a 3' genomic locus fragment, but which differs in that none of the coding sequence is omitted and thus the 5' and the 3' genomic fragments used were initially contiguous before being disrupted by the introduction of the nucleic acid encoding the positive selectable marker gene. This "knock-in" type of construct is thus very useful for the construction of mutant transgenic animals when only a limited region of the genomic locus of the gene to be mutated, such as a single exon, is available for cloning and genetic manipulation. Alternatively, the "knock-in" construct can be used to specifically eliminate a single functional domain of the targeted gene, resulting in a transgenic animal which expresses a polypeptide of the targeted gene which is defective in one function, while retaining the function of other domains of the encoded polypeptide. This type of "knock-in" mutant frequently has the characteristic of a so-called "dominant negative" mutant because, especially in the case of proteins which homomultimerize, it can specifically block the action of (or "poison") the polypeptide product of the wild-type gene from which it was derived. In a variation of the knock-in technique, a marker gene is integrated at the genomic locus of interest such that expression of the marker gene comes under the control of the transcriptional regulatory elements of the targeted gene. One skilled in the art will be familiar with useful markers and the means for detecting their presence in a given cell.

As mentioned above, the homologous recombination of the above described "knock out" and "knock in" constructs is sometimes rare and such a construct can insert nonhomologously into a random region of the genome where it has no effect on the gene which has been targeted for deletion, and where it can potentially recombine so as to disrupt another gene which was otherwise not intended to be altered. Such non-homologous recombination events can be selected against by modifying the above-mentioned targeting vectors so that they are flanked by negative selectable markers at either end (particularly through the use of two allelic variants of the thymidine kinase gene, the polypeptide product of which can be selected against in expressing cell lines in an appropriate tissue culture medium well known in the art—i.e. one containing a drug such as 5-bromodeoxyuridine). Non-homologous recombination between the resulting targeting vector comprising the negative selectable marker and the genome will usually result in the stable integration of one or both of these negative selectable marker genes and hence cells which have undergone non-homologous recombination can be selected against by growth in the appropriate selective media (e.g. media containing a drug such as 5-bromodeoxyuridine for example). Simultaneous selection for the positive selectable marker and against the negative selectable marker will result in a vast enrichment for clones in which the knock out construct has recombined homologously at the locus of the gene intended to be mutated. The presence of the predicted chromosomal alteration at the targeted gene locus in the resulting knock out stem cell line can be confirmed by means of Southern blot analytical techniques which are well known to those familiar in the art. Alternatively, PCR can be used.

Each targeting vector to be inserted into the cell is linearized. Linearization is accomplished by digesting the DNA with a suitable restriction endonuclease selected to cut only within the vector sequence and not the 5' or 3' homologous regions or the selectable marker region.

For insertion, the targeting vector is added to the ES cells under appropriate conditions for the insertion method chosen, as is known to the skilled artisan. For example, if the ES cells are to be electroporated, the ES cells and targeting vector are exposed to an electric pulse using an electroporation machine and following the manufacturer's guidelines for use. After electroporation, the ES cells are typically allowed to recover under suitable incubation conditions. The cells are then screened for the presence of the targeting vector as explained herein. Where more than one construct is to be introduced into the ES cell, each targeting vector can be introduced simultaneously or one at a time.

After suitable ES cells containing the knockout construct in the proper location have been identified by the selection techniques outlined above, the cells can be inserted into an embryo. Insertion may be accomplished in a variety of ways known to the skilled artisan, however the typical method is by microinjection. For microinjection, about 10-30 cells are collected into a micropipet and injected into embryos that are at the proper stage of development to permit integration of the foreign ES cell containing the recombination construct into the developing embryo. For instance, the transformed ES cells can be microinjected into blastocytes. The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan.

While any embryo of the right stage of development is suitable for use, typical embryos are male. In mice, the typical embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2-3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the CMAH gene knocked out in various tissues of the offspring by probing the Western blot with an antibody against the particular CMAH protein, or an antibody against the marker gene product (i.e., the presence of Neu5GC using an antibody as identified in PCT application no. PCT/US2004/022415, incorporated herein by reference in its entirety). Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of an OAT gene can be controlled by recombinase sequences.

Animals containing more than one knockout construct and/or more than one transgene expression construct are prepared in any of several ways. A typical manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

In another aspect, a transgenic animal can be obtained by introducing into a single stage embryo a targeting vector. The zygote is the best target for micro-injection. In the mouse, the male pronucleus reaches the size of approximately 20 micrometers in diameter which allows reproducible injection of 1-2 pl of DNA solution. The use of zygotes as a target for gene transfer has an advantage in that in most cases the injected DNA will be incorporated into the host gene before the first cleavage (Brinster et al. (1985) PNAS 82:4438-4442). As a consequence, all cells of the transgenic animal will carry the incorporated nucleic acids of the targeting vector. This will in general also be reflected in the efficient transmission to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus. In some species such as mice, the male pronucleus is typically used. Typically the exogenous genetic material be added to the male DNA complement of the zygote prior to its being processed by the ovum nucleus or the zygote female pronucleus. It is thought that the ovum nucleus or female pronucleus release molecules which may affect the male DNA complement, perhaps by replacing the protamines of the male DNA with histones, thereby facilitating the combination of the female and male DNA complements to form the diploid zygote.

Thus, the exogenous genetic material is typically added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the a exogenous nucleic acid (e.g., a targeting vector) into the embryo may be accomplished by any means known in the art such as, for example, microinjection, electroporation, or lipofection. Following introduction of the exogenous nucleic acid into the embryo, the embryo may be incubated in vitro for varying amounts of time, or reimplanted into the surrogate host, or both. In vitro incubation to maturity is within the scope of this invention. One common method in to incubate the embryos in vitro for about 1-7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is used. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of a transgene (e.g., the exogenous genetic material or targeting vector constructs) which are added to the zygote is dependent upon the total amount of exogenous genetic material added and will be the amount which enables the genetic transformation to occur. Theoretically only one copy is required; however, generally, numerous copies are utilized, for example, 1,000-20,000 copies of a targeting vector construct, in order to insure that one copy is functional.

Reimplantation is accomplished using standard methods. Usually, the surrogate host is anesthetized, and the embryos are inserted into the oviduct. The number of embryos implanted into a particular host will vary by species, but will usually be comparable to the number of offspring the species naturally produces.

Transgenic offspring of the surrogate host may be screened for the presence and/or expression of an exogenous polynucleotide (e.g., that of a targeting vector) by any suitable method as described herein. Alternative or additional methods include biochemical assays such as enzyme and/or immunological assays, histological stains for particular marker or enzyme activities, flow cytometric analysis, and the like.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different knockout, or both. Alternatively, the partner may be a parental line. Where in vitro fertilization is used, the fertilized embryo may be implanted into a surrogate host or incubated in vitro, or both. Using either method, the progeny may be evaluated using methods described above, or other appropriate methods.

Retroviral infection can also be used to introduce a targeting vector into a non-human animal. The developing non-human embryo can be cultured in vitro to the blastocyst stage. During this time, the blastomeres can be targets for retroviral infection (Jaenich, R. (1976) PNAS 73:1260-1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the targeting vector is typically a replication-defective retrovirus carrying the exogenous nucleic acid (Jahner et al. (1985) PNAS 82:6927-6931; Van der Putten et al. (1985) PNAS 82:6148-6152). Transfection is easily and efficiently obtained by culturing the blastomeres on a monolayer of virus-producing cells (Van der Putten, supra; Stewart et al. (1987) EMBO J. 6:383-388). Alternatively, infection can be performed at a later stage. Virus or virus-producing cells can be injected into the blastocoele (Jahner et al. (1982) Nature 298:623-628). Most of the founders will be mosaic for the targeting vector (e.g., the exogenous nucleic acids) since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

The cre-lox system, an approach based on the ability of transgenic mice, carrying the bacteriophage Cre gene, to promote recombination between, for example, 34 bp repeats termed loxP sites, allows ablation of a given gene in a tissue specific and a developmentally regulated manner (Orban et al. (1992) PNAS 89:6861-6865). LoxP sites can be placed flanking an exon of any given gene. Thus, transgenic mice carrying the Cre gene under the control of a selected promoter can be crossed with transgenic mice carrying a transgene flanked by loxP sites to generate doubly transgenic mice. The pioneering work in developing this system was carried out by Orban et al. (1992) PNAS 89:6861-6865. In one embodiment, the invention uses this technology to target specific tissues in mice (e.g., expressing CMAH), in a developmentally regulated fashion in order to produce a mouse lacking Neu5Gc.

Gene targeting producing gene knock-outs allows one to assess in vivo function of a gene which has been altered and used to replace a normal copy and to generate knockout animals with utility as food. The modifications include insertion of mutant stop codons, the deletion of DNA sequences, or the inclusion of recombination elements (lox p sites) recognized by enzymes such as Cre recombinase. The Cre-lox system as used in one embodiment of the present invention allows for the ablation of a given gene or the ablation of a certain portion of the gene sequence. The Cre-lox system was used to generate CMAH knockout mice exhibiting reduced Neu5GC.

In another aspect, the invention relates to the use of an CMAH knockout animal, in particular an animal used for food stuff to generate food, food products, pharmaceuticals, and biologics for use.

In a further embodiment, the invention relates to cells and tissues that carry mutations in CMAH. The cells can be primary cells or established cell lines obtained from the transgenic animals of the invention according to routine methods, i.e. by isolating and disintegrating tissue.

Such cells and tissues derived from the animals of the invention, in which the activity of CMAH has been reduced or abolished, are useful in in vitro methods relating to the study of sialic acid moieties, binding and diseases and disorders related thereto.

Cells and cell lines derived from the knockout animals are further useful in screening systems. The invention demonstrates that knockout of CMAH results specific decreases of Neu5Gc. No obvious morphological defects were noted in CMAH knockout mice.

EXAMPLES

Example 1

Neu5Gc and Neu5Ac were respectively purchased from Inalco Spa (Milano, Italy) and Pfanstiehl Laboratories, Inc (Waukegan, Ill.). 1,2-diamino-4,5-methylene dioxybenzene (DMB), Chlorpromazine, Genistein, Nystatin, Amiloride, and Saponin were from Sigma-Aldrich (St Louis, Mo.). Premium Human Serum type AB was from Irvine Scientific (Santa Ana, Calif.). Neu5Ac aldolase came from ICN (Costa Mesa, Calif.). All the reagents used were HPLC grade.

Cell Lines—

Caco-2 cells (human epithelial cells isolated from a primary colon carcinoma), normal human skin fibroblasts (CCD-919-SK) and Chinese Hamster Ovary (CHO-K1) cells were purchased from ATCC (Manassas, Va.). Mutant human skin fibroblasts (GM05520, GM08496 and GM01718) were obtained from the Coriell Institute for Medical Research (Camden, N.J.). Chimpanzee Fred and human LB EBV-transformed lymphoblasts were a gift from Dr. Peter Parham, Stanford University.

Cell Culture—

Caco-2 cells were propagated in alpha-MEM containing Glutamax™ and a mixture of ribonucleosides and deoxyribonucleosides (Gibco/Invitrogen) supplemented with 20% FCS. All the fibroblast cell lines and CHO-K1 cells were cultured in the same media supplemented respectively with 15% non-heat inactivated FCS or 10% heat-inactivated FCS. Chimpanzee Fred and human LB EBV-transformed lymphoblasts were cultured in RPMI-1640 (Gibco/Invitrogen) supplemented with 10% heat inactivated FCS or 15% human serum. All the cultures were maintained at 37° C., 5% $CO_2$ atmosphere. In order to deplete any remaining Neu5Gc from FCS, the cells were split and cultured, prior to Neu5Gc feeding experiments, for at least 4 days in alpha-MEM supplemented with an adequate percentage of heat-inactivated premium human serum instead of FCS. The cells were then maintained under the same conditions during the whole feeding experiment. The human serum was heat inactivated at 56° C. for 30 min before use.

Preparation of ManNGc from Neu5Gc—

ManNGc was prepared by incubating 73 µmoles of Neu5Gc with 624 U Lactate dehydrogenase, 30 µmoles NADH and 10 U Neu5Ac Aldolase, EC 4.1.3.3, in 15 ml of 100 mM Potassium phosphate buffer, pH 7.2. The incubation was carried out at 37° C. for 16 h. The ManNGc was separated from any unreacted Neu5Gc by passing the product serially over AG50WX-2 and AG1X-8 (Bio-Rad, Richmond, Calif.) ion-exchange resins as previously described. The run-through and 5 column-volumes of water washes were collected and concentrated by freeze-drying. The reaction yield (91-98%) was followed by the disappearance of Neu5Gc, using DMB derivatization of the reaction mixture and analysis by HPLC (see protocol described below).

Preparation and Purification of Sia from Bovine Submaxillary Mucin—

A mixture of standard Sias were prepared from bovine submaxillary mucin. Total mucins were extracted from frozen submaxillary glands as previously described. Sias then were released with mild acid, collected by dialysis (1000 daltons molecular-weight-cut-off) and purified on ion exchange columns, under conditions determined to minimize loss of O-acetylation.

Neu5Gc and ManNGc Feeding Experiment—

Neu5Ac, Neu5Gc or ManNGc were dried, dissolved in the appropriate media supplemented with heat-inactivated human serum, sterilized using a Spin-X® (Corning Inc., Corning, N.Y.) and then added to the cells. The pH of the media containing Sia, was adjusted to neutrality using sterilized 1 M NaOH before starting the feeding experiment. Cells were cultured in the presence of up to 3 mM free Sia or ManNGc for 1 or 3 days at 37° C. At the end of the feeding, cells were washed with cold PBS, harvested either by scraping or with 2 mM EDTA for fibroblasts, and washed again with cold PBS prior to fractionation.

Fractionation of the Labelled Cells—

Washed cell pellets were sonicated into 500 µL of 20 mM sodium phosphate buffer or 20 mM Tris-HCl, pH 7.5, using 4×15 second pulses of a sonicator cell disrupter, model Sonic Dismembrator (Fisher Scientific) at a probe setting of 3. The sonicate was centrifuged at 75×g for 15 min, and the pellet obtained consisted primarily of nuclei and unbroken cells. The pellet contained <5% of the incorporated sialic acid, as determined using a radioactive tracer (data not shown). The supernatant was therefore considered as the "Total Homogenate" fraction. A portion (20%) of the "Total Homogenate" fraction was taken for protein quantification and Sia analysis by DMB derivatization and HPLC analysis (See protocol below). The remainder was centrifuged at 100,000×g for 1 h. The resulting pellet, called the "membrane" fraction, was then resuspended by sonication (15 sec) in 200 µL of sodium acetate buffer, pH 5.5. The 100,000×g supernatant, called the "soluble" fraction was adjusted to 90% ethanol using absolute ice-cold ethanol, and placed overnight at −20° C. The flocculant precipitate, which represents the "soluble protein" fraction, was washed 3 times with 90% of ice-cold ethanol and then, resuspended in 200 µL of water. The supernatant fluid representing the cytosolic low molecular weight (LMW) fraction was dried and brought up in 100 µL with water prior to Sia analysis. All the Sias in these fractions were released with mild acid hydrolysis if necessary and then analysed by HPLC, after DMB derivatization. Protein quantification was performed on the total homogenate, membrane and soluble protein fractions by using the BCA protein assay kit from Pierce (Rockford, Ill.). In some experiments, the resulting data obtained for the Sia bound to the membrane fraction and to the soluble proteins were pooled and presented here as a High Molecular Weight (HMW) fraction.

Sialic Acid Release, DMB Derivatization and HPLC Analysis—

The bound Sias from the total homogenate, membrane and soluble protein fractions were released using 2M acetic acid hydrolysis, 3 h at 80° C. The released Sias, or free Sias contained in the soluble LMW fraction were passed through a Microcon® YM-10 (Millipore, Bedford, Mass.) prior to DMB derivatization, which was done according to Hara et al., 1989. DMB-Sia derivatives from the different fractions were then analysed by HPLC using a C18 column (Microsorb MV-TM 100 A, Varian). Isocratic elution was achieved using 7% Methanol, 8% Acetonitrile in water during 50 min at 0.9 ml/min flow. The eluant was monitored by fluorescence as described.

Quantification of Sias—

For all HPLC chromatograms, the quantification of Sias was done by comparison with known quantities of DMB derivatized Neu5Gc and Neu5Ac used as standards and then reported in terms of pmoles of Sia. For total homogenate, membrane and cytosolic protein fractions, this number was expressed per mg of protein. Due to minor sample-to-sample variations in amounts and recoveries, the data in the Figures is presented as percent of Neu5Gc over total Sias, rather than as absolute amounts.

MS and MS/MS Analysis of DMB Derivatives—

In some experiments, the nature of the DMB derivatives of Sias was confirmed by mass spectrometry on a Finnigan MAT HPLC with online mass spectrometry system using a model LCQ-Mass Spectrometer System A. A Varian C18 column was used and eluted in the isocratic mode with 8% acetonitrile, 7% methanol, 0.1% formic acid in water at 0.9 ml/min over 50 min. The eluant was simultaneously monitored by UV absorbance at 373 nm and by Electrospray Ionization mass spectrometry. The ESI settings used were capillary temperature of 210° C., capillary voltage at 31 V and the lens offset voltage at 0 V. Spectra were acquired by scanning from m/z 150-2000 in the positive ion mode. In some instances, MS/MS was acquired by selecting the parent mass and using a 20% normalized collision energy. Data analysis was performed using the XCALIBUR data analysis program from the instrument manufacturer.

Endocytosis Inhibition Experiments—

Caco-2 or normal fibroblast cells were split and cultured in alpha-MEM media supplemented respectively with 20% or 15% human serum for 4 days before starting the endocytosis drug inhibition experiments, in order to deplete any Neu5Gc derived from FCS. Cells were then pre-treated for 2 h with the specific inhibitors, under the same culture conditions. Fresh media containing the same amount of inhibitor and 3 mM of Neu5Gc was then added to the cells, which were incubated for 16 h or 3 days and finally harvested and fractionated as described above. Based on prior literature, Chlorpromazine, Genistein, Nystatin and Amiloride were used at final concentrations of 6 µg/mL, 200 µM, 25 µg/mL and 3 mM, respectively.

Western Blot Analysis—

Membrane proteins extracted from Neu5Gc-fed, ManNGc-fed or non-fed human wild-type (WT) and mutant fibroblasts were separated by SDS-PAGE electrophoresis using an 8% polyacrylamide gel. The separated proteins were transferred onto nitrocellulose membrane, which was blocked overnight with Tris Buffer Saline containing 0.1% of Tween-20 (TBS-T). Immunodetection was then performed by using our recently described anti-Neu5 Gc antibody (1:10,000 in TBS-T, 3 h, room temperature (RT)). Binding of the anti-Neu5Gc antibody was detected using a secondary HRP-conjugated donkey anti-chicken IgY antibody diluted at 1:30,000 in TBS-T for 45 min at RT (Jackson ImmunoResearch Laboratories, West Grove, Pa.). Final development of the blots was performed by using Supersignal West Pico ECL reagent (Pierce, Rockford, Ill.) and X-OMAT Kodak films.

Flow Cytometry—

Human WT and mutant fibroblasts, grown in media with 10% FCS+20% horse serum for 3 days, were lightly trypsinized (0.04% trypsin, 0.53 mM EDTA for 5 min) to release cells from the flasks. The cells were washed with PBS and then fixed overnight with 1% paraformaldehyde in PBS. Fixed cells were permeabilized or not with 0.1% saponin in PBS at RT for 20 mM. Chicken anti-Neu5Gc antibody was added to cells at a 1:200 dilution in PBS and incubated at RT for 30 min. Cells were then washed with PBS and resuspended in FITC-conjugated goat anti-chicken IgY (1 µg/100 µl) (Southern Biotechnology Associates, Birmingham, Ala.) and allowed to incubate for 30 min at RT. Labelled cells were washed with PBS and resuspended in 500 µl PBS for analysis of FITC fluorescence on a FACS Calibur (BD Biosciences, San Jose, Calif.).

Fluorescence Microscopy—

Human WT and mutant fibroblasts were grown on poly-D-lysine-coated glass Chamber Slides (Nalge Nunc International, Naperville, Ill.) with media containing 10% FCS+20% horse serum for 4 days. Cells were fixed onto slides using 1% paraformaldehyde in PBS for 30 mM at RT before permeabilizing with 0.1% saponin for 20 min at RT. Chicken anti-Neu5Gc antibody was then added at 1:50 dilution in PBS along with 1 µg of mouse anti-LAMP-1 (clone H4A3, BD Pharmingen, San Diego, Calif.) and incubated at RT for 1 h. Bound antibodies were then detected with FITC-goat anti-chicken IgY and Cascade Blue-goat anti-mouse IgG (each at 1 µg/100 µl) at RT for 1 h. Cells were washed with PBS and covered with Gel/Mount (Biomedia, Foster City, Calif.) before fluorescence imaging with a Zeiss Microscope at 400× magnification with emission filters at 400 and 520 nm for Cascade Blue and FITC, respectively.

Figure 1:
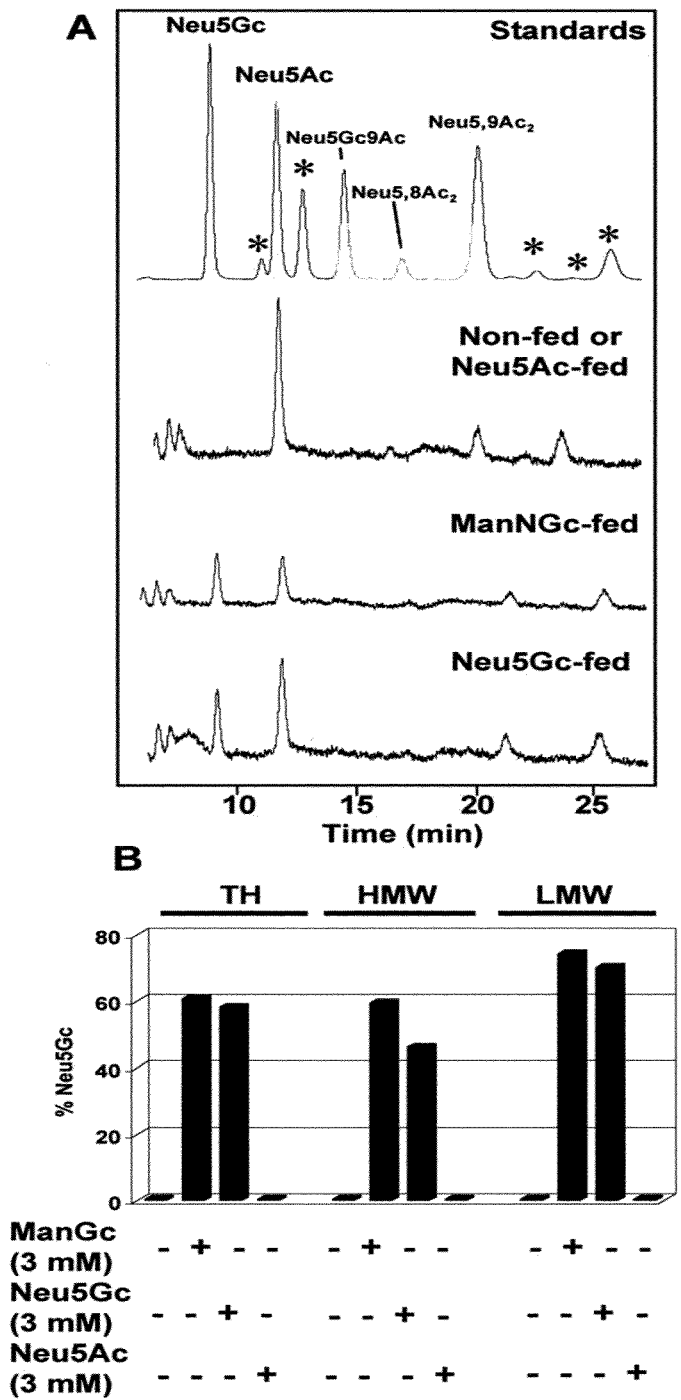
FIG. 1 depicts the incorporation of free Neu5Gc in human epithelial cells. Caco-2 cells were fed or not fed for 3 days, with Neu5Gc, ManNGc or Neu5Ac, each at 3 mM final concentration. The cells were harvested and fractionated, and the Sia content of the different fractions was analysed by DMB derivatization and LC-MS analysis as described in "Experimental Procedures". (A) DMB-HPLC profiles of Sia released from membrane fractions. Peaks indicated by an asterisk (*) respectively correspond to Neu5Gc7Ac, Neu5,7Ac$_2$, Neu5,8,9Ac$_3$, Neu5Gc7,9Ac$_2$, Neu5,7,9Ac$_3$. MS and MS/MS data for the peaks corresponding to DMB-Neu5Gc and DMB-Neu5Ac from the membrane bound Sia of ManNGc and Neu5Gc-fed Caco-2 cells were obtained (not shown, see text for discussion) (B) Proportion of Neu5Gc (expressed as percent of total Sia) in the different fractions of Caco-2 cells. Quantitative information (pmol Sia per mg protein) can be found in a "Supplemental Data" file. TH: Total homogenate; HMW: High Molecular Weight fraction, LMW: Cytosolic LMW fraction.

Free Neu5Gc can be taken up by human epithelial cells from an exogenous source and incorporated into different subcellular fractions. Evidence was presented suggesting that the small amounts of Neu5Gc found in some human tissues originated from dietary sources and showed that human Caco-2 cells (human epithelial cells from a primary colon carcinoma) in culture could metabolically incorporate free Neu5Gc, as determined by a Western blot of a total homogenate, using and anti-Neu5Gc antibody. Increasing incorporation of Neu5Gc was found in the total homogenate fraction of the cells over time, with the highest level reached after incubation with 3 mM Neu5Gc for 3 days. Moreover, Western blotting with an anti Neu5Gc antibody demonstrated metabolic incorporation of Neu5Gc into glycoproteins of these cells. The partitioning of the exogenous Neu5Gc into different subcellular fractions of these cells has now been studied. Prior to feeding, Caco-2 cells were split and cultured in human serum instead of FCS, in order to eliminate traces of Neu5Gc in the cells. Culture was continued for 3 days in the presence of 3 mM Neu5Gc, using 3 mM ManNGc and Neu5Ac as positive controls. Indeed, it has already been shown that Neu5Ac and ManNGc can be incorporated into cells and that ManNGc or its peracetylated form can be metabolized into Neu5Gc. After the 3 day feeding, the cells were harvested and the Neu5Gc content of the different subcellular fractions analyzed by DMB derivatization, HPLC, MS and MS/MS analysis. As shown in FIG. 1A, the DMB-HPLC profiles of Sias released from the membranes of Caco-2 cells fed with 3 mM ManNGc or Neu5Gc presented two peaks which correspond to Neu5Gc and Neu5Ac, by comparison with the retention times of standards. Cells that were not fed or fed with Neu5Ac had only one peak corresponding to Neu5Ac. These results were confirmed by LC-MS and MS/MS analysis. DMB-Neu5Gc and DMB-Neu5Ac adducts gave signals at m/z 442, 424 and 426, 408 respectively, representing molecular ions of DMB-derivatized Neu5Gc and Neu5Ac and their dehydrated forms. LC-MS and MS/MS data obtained on DMB-derivatized Sias released from the membranes of Caco-2 cells non-fed or fed with Neu5Ac gave only a single ion at m/z 426 which can be broken down to 408 by MS/MS, confirming the presence of Neu5Ac and the absence of Neu5Gc. The same analysis on Neu5Gc or ManNGc fed Caco-2 cell membrane Sias gave ions at m/z 442 and 426, which are respectively dehydrated to 424 and 408 in MS/MS analysis. These analyses confirmed the presence of Neu5 Gc associated specifically within the glycoconjugates of the membranes of Caco-2 cells fed with ManNGc or Neu5Gc. All other sub-cellular fractions were also studied using the same DMB-HPLC approach. Due to sample-to-sample variations in amounts and recoveries, we present the data in this and subsequent figures as percent of Neu5Gc over total Sias, rather than as absolute amounts. FIG. 1B summarizes the results showing that the total homogenate (TH), High Molecular Weight fraction (HMW is the combination of membrane and soluble protein fractions) and cytosolic Low Molecular Weight (LMW) fraction contain 58, 46 and 70% Neu5Gc respectively. In the experiment presented here, the % of Neu5Gc in the membrane fraction of cells fed with Neu5Gc was lower compared to the one obtained for cells fed with ManNGc. This was not always the case, as was observed in other feeding experiments that free Neu5Gc can be as efficient as ManNGc and sometimes even better. The relative percentages obtained for the other fractions (total homogenate, LMW and soluble protein) were similar in several repeated ManNGc and Neu5Gc feeding experiments.

Figure 2:
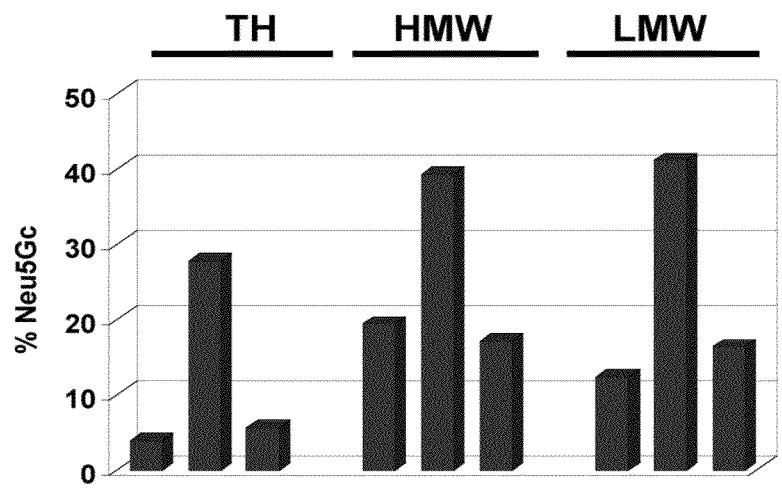
FIG. 2 depicts free Neu5Gc taken up and incorporated into other types of human cells. Human fibroblast and neuroblastoma cells were fed or not, for 3 days with 3 mM Neu5Gc or Neu5Ac, and the cells then harvested and fractionated as described in "Experimental Procedures". The Sia content in the different fractions of the cells were analysed by DMB derivatization followed by HPLC. The proportion of Neu5Gc (expressed as percent of total Sia) of the different fractions from (A) human fibroblasts or (B) human neuroblastomas is shown. TH: Total homogenate; HMW: High Molecular Weight fraction, LMW: Cytosolic LMW fraction.
Figure 2:
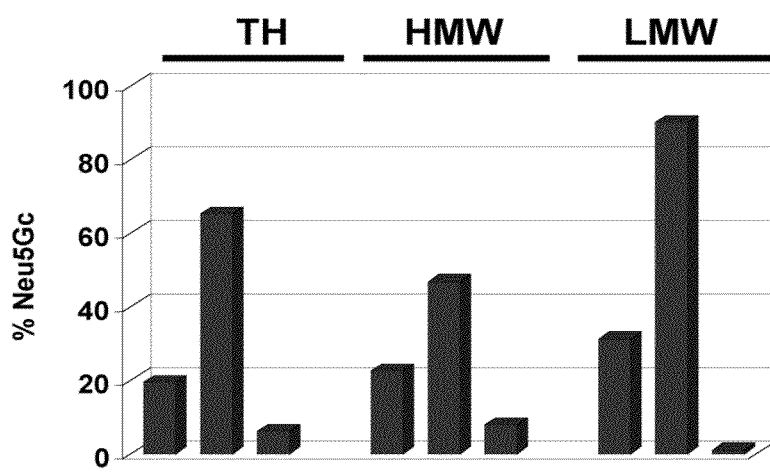

The uptake mechanism of free Neu5Gc is not specific for human epithelial cells. The above experiments showed that free Neu5Gc can be taken up by human epithelial carcinoma cells from the media, and incorporated into different subcellular fractions such as membrane-bound glycoconjugates, soluble proteins, and low molecular weight compounds present in the cytosol. To see if this is a specialized mechanism in human carcinoma cells, similar Neu5Gc feeding experiments were done on other human cell types such as normal skin fibroblasts and neuroblastomas. It was found that fibroblast cells can also take up free Neu5Gc from the media, albeit in a less efficient manner. As presented in FIG. 2A, 28%, 39% and 41% Neu5Gc are present in the TH, HMW and cytosolic LMW fractions of the human normal fibroblasts after Neu5Gc feeding. Lower levels (4%, 19%, 12% Neu5Gc) were already present in the same fractions when fibroblast cells were not incubated in presence of 3 mM Neu5Gc. This Neu5Gc is assumed to be derived from Neu5Gc on FCS glycoproteins used for cell culture, prior to feeding experiments (see below). Human neuroblastoma cells could also incorporate Neu5Gc with an efficiency comparable to the Caco-2 cells (FIG. 2B). These data indicate that the uptake mechanism of Neu5Gc can also occur in other human cell types, with varying efficiencies.

The Uptake Mechanism of Free Neu5Gc is not Specific for Human Cells.

To ask if the uptake mechanism of free Neu5Gc is specific for human cells, Neu5Gc feeding of human and chimpanzee lymphoblasts was compared. Humans are evolutionarily most closely related to the chimpanzee, whose proteins are ~99% identical to those of humans. Of course, great apes such as chimpanzees are able to express Neu5Gc in large amounts because they have an active form of the CMP-Neu5Ac hydroxylase. Prior to the feeding experiment, both cell types were split and cultured in human serum instead of FCS for a couple of weeks. As expected, the Neu5Gc content of chimpanzee lymphoblasts could not be eliminated completely because of the endogenous production of Neu5Gc. After a 3 day feeding of 3 mM Neu5Gc or Neu5Ac, the cells were harvested, fractionated and, the Neu5Gc content of the different subcellular fractions were analysed. As shown in the FIG. 3A, the human cells fed with 3 mM Neu5Gc contained 67% Neu5Gc in the TH, 51% in the HMW fraction and 80% in the LMW cytosolic compounds. In contrast, the same cells had almost no detectable Neu5Gc when they were non-fed or fed with Neu5Ac (FIG. 3A). With chimpanzee cells, we measured baseline levels at 57% Neu5Gc in the TH, 66% in the HMW fraction and 70% in the LMW fraction of non-fed cells (FIG. 3B), representing the endogenous production of Neu5Gc by these cells, When the chimpanzee lymphoblasts were fed with 3 mM Neu5Ac, the percentages of Neu5Gc present in the different fractions changed only minimally (FIG. 3B), presumably because of biosynthetic transformation of Neu5Ac to Neu5Gc occurring at the sugar nucleotide level. When the chimpanzee lymphoblasts were fed with 3 mM Neu5Gc, we observed an increase above the baseline levels, to 70% for the TH, 72% for the HMW fraction and 84% for the LMW fraction (FIG. 3B). Similar experiments have been done with CHO-K1 cells and with epithelial cells isolated from a spontaneous tumor from a CMAH gene knock out mouse. Since all these experiments gave similar results, we can conclude that the uptake mechanism of Neu5Gc is not specific for human cells but can also take place in other mammalian cells. However, since non-human cells often have large endogenous amounts of Neu5Gc, the consequences are more dramatic in human cells.

Free Neu5Ac and Neu5Gc are Taken Up and Incorporated by the Same Pathways.

Figure 4:
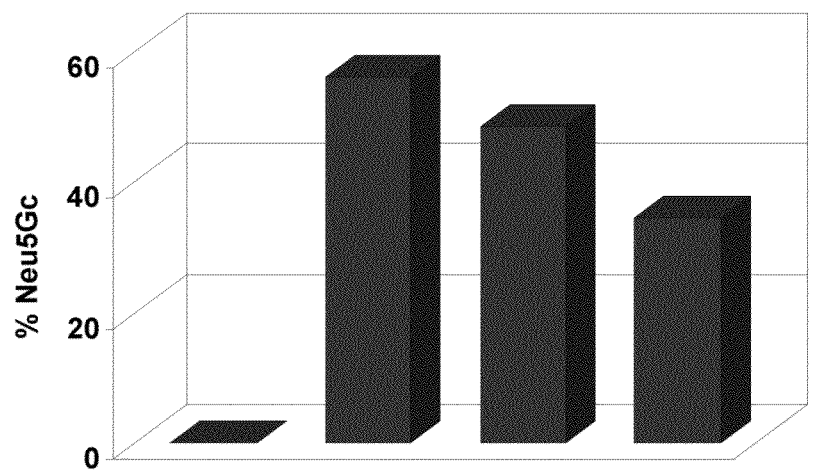
FIG. 4 depicts free Neu5Ac can compete with the incorporation of free Neu5Gc. Caco-2 cells grown in human serum, were fed for 3 days with 3 mM Neu5Gc with or without addition in the media of Neu5Ac at 3 mM or 15 mM final concentration. The cells were then harvested, fractionated and the Sia content in the different fractions analysed by DMB derivatization followed by HPLC. The proportion of Neu5Gc (expressed as percent of total Sia) of (A) total homogenate fraction and (B) membrane fraction is shown.
Figure 4:
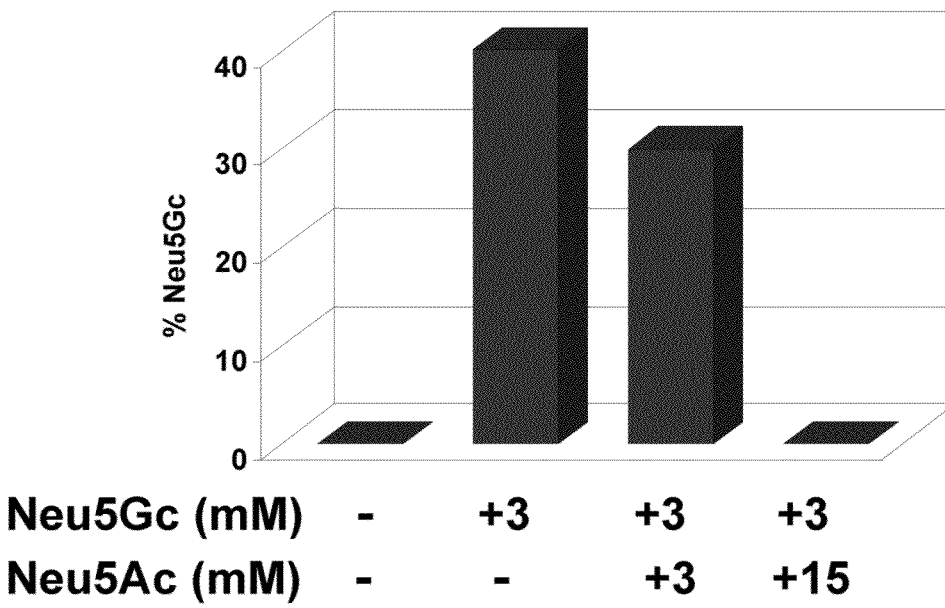

From these data and from other recent reports in the literature, it is concluded that Neu5Ac and Neu5Gc can be taken up by many kinds of cells from an exogenous source and incorporated into endogenous glycoconjugates. Several prior studies indicate that Neu5Gc and Neu5Ac are used interchangeably by essentially all of the steps leading to their final incorporation into glycoconjugates. Higa and Paulson showed that CMP-Sia synthetases from calf brain and from bovine and equine submaxillary glands both converted Neu5Ac and Neu5Gc to their CMP derivatives efficiently. They also studied six mammalian sialyltransferases purified from porcine, rat, and bovine tissues and concluded that CMP-NeuAc and CMP NeuAc were equally good donor substrates for all the enzymes. Schauer and colleagues showed that the frog liver CMP-Sia synthetases had very similar Km values for Neu5Ac and Neu5Gc. In our own prior work we concluded that CMP-Neu5Gc and CMP-Neu5Ac could be taken up by Golgi vesicles and incorporated into the endogenous glycoproteins at an approximately equal rate. Similar observations were made by Lepers etc al. in rat and mouse liver Golgi. Thus, by doing competition experiments in Caco-2 and human normal fibroblast cells we could determine whether Neu5Gc and Neu5Ac are taken up and incorporated via the same pathways. Both cell lines gave similar results, and only the results for Caco-2 cells are presented in FIG. 4. Feeding was done for 3 days with 3 mM Neu5Gc in the absence or presence (3 mM or 15 mM) of Neu5Ac in the media. The baseline incorporation of 56% Neu5Gc in the TH was reduced to 48% in the presence of 3 mM Neu5Ac and further decreased to 35% in the presence of added 15 mM Neu5Ac (FIG. 4A). The percentage of Neu5Gc was even more affected in the membrane-bound fraction, reducing from 41% to 29.9% with 3 mM Neu5Ac, and almost to zero in the presence of 15 mM Neu5Ac (FIG. 4B). Since a 5-fold excess of Neu5Ac was enough to abolish the incorporation of Neu5Gc into the membrane fraction of the cells, it is concluded that both molecules likely use the same pathways to enter into human cells and become available for metabolic incorporation. It is of course possible that there are minor differences in utilization of Neu5Gc and Neu5Ac by various enzymes and transporters in the pathways.

Free Neu5Gc Enters into Cells Via Pathways of Endocytosis.

Negatively charged hydrophilic molecules like sialic acids usually do not cross membranes. To understand how free Neu5Gc enters into cells, we explored the hypothesis that it does so via endocytic pathways. Thus, Neu5Gc feeding experiments on Caco-2 cells were done in the presence of drugs that are known to inhibit various endocytic pathways common to most cell types. Based on literature, it was decided to use Chlorpromazine for blocking the clathrin dependent pathway and Nystatin and Genistein for the clathrin independent pathways (with an additional specific action of Nystatin on caveolar uptake). Amiloride was used as an inhibitor of fluid phase pinocytosis. All these drugs were used at concentrations described in the Experimental Procedures and based on prior literature. As before, the Caco-2 cells were incubated in an appropriate media containing human serum instead of FCS and pre-treated with the drug for 2 hours, followed by the addition of 3 mM of Neu5Gc for 16 h or 3 days. As shown in FIG. 5A, incorporation of Neu5Gc in the TH fraction, in the presence of Chlorpromazine and Nystatin (~65% in both cases) was about the same as for the non-treated Caco-2 cells. In contrast, Neu5Gc incorporation into cells was decreased in the presence of Genistein (51%) and much further by Amiloride (35.4% Neu5Gc). Analysis of incorporation into membrane-bound glycoconjugates gave similar results: while there was no obvious difference in the Neu5Gc incorporation for cells cultured without (45%) or with Chlorpromazine (50%) or with Nystatin (44%), Genistein and Amiloride caused marked reduction of incorporation to 34% and 10% respectively. These results indicate that exogenous free Neu5Gc enters cells via clathrin-independent endocytic pathways with a major contribution from fluid phase pinocytosis.

The Lysosomal Sialic Acid Transporter is Required for Export of Free NeuGc from the Lysosome to the Cytosol.

Free Neu5Gc molecules entering the cell via endocytic pathways would still be restricted from passively diffusing out of endosomes into the cytosol. We hypothesized that they would eventually reach the lysosome, where they would have the opportunity to utilize the previously known lysosomal sialic acid transporter (58-60) to reach the cytosol. To test this hypothesis, fibroblasts from a patient (GM05520) with a severe infantile form (ISSD) of sialic acid storage disease, a disease that is caused by a genetic defect in this transporter, were used. As shown in FIG. 6, the present of Neu5Gc incorporation into membrane-bound glyconconjugates was reduced from 37% in normal wild-type (WT) fibroblasts to 5% in these mutant cells. As a control, the metabolic conversion of ManNGc into Neu5Gc in these cells was also studied, which presumably occurs following passive diffusion through the plasma membrane, and does not require the lysosomal sialic acid transporter. As predicted, it was found that there was essentially no difference in between normal (19% Neu5Gc) versus mutant fibroblasts (18% Neu5Gc) following feeding with 3 mM ManNGc. Another similar mutant human fibroblast cell line (GM08496) was studied, with a partial inhibition of function of the lysosomal sialic acid transporter. This cell line was isolated from a patient suffering from Salla disease, a milder adult form of sialic acid storage disease. Neu5Gc feeding of these cells resulted in 16% Neu5Gc in membrane-bound glycoconjugates in comparison to the 37% seen in normal WT fibroblasts. Again, feeding with ManNGc gave no obvious change from the control (17% Neu5Gc). To further confirm that there was a difference in incorporation into glycoproteins, a Western blot analysis was carried out of proteins extracted from the membranes of wild-type and GM05520 mutant human fibroblasts using an anti-Neu5Gc antibody, with or without prior Neu5Gc or ManNGc feeding. As shown in FIG. 6B, the mutant fibroblasts could not incorporate Neu5Gc into glycoproteins, but could in fact convert it from ManNGc. Taken together, the data confirm the hypothesis that the lysosomal sialic acid transporter plays a crucial role in delivering free sialic acids, that enter into cells via endocytosis to the cytosol, for activation and incorporation into glycoconjugates.

Both the Lysosomal Sialidase and the Lysosomal Sialic Acid Transporter are Required for Incorporation of Glycoprotein-Bound NeuGc into Human Cells.

Several studies (including this one) have shown that when human cells are transferred from conventional media containing FCS into serum-free media or human serum, the small amounts of endogenous Neu5Gc in these cells gradually disappear. It has always been assumed that this is because FCS contains many glycoproteins with attached Neu5Gc. However, the pathway by which these glycosidically-bound Neu5Gc molecules enter the cell and eventually become incorporated into endogenous glycoproteins has never been defined. This question is also of direct relevance to human gut epithelial cells, which would be exposed to glycoprotein-bound Neu5Gc of dietary origin (red meat, milk products for example). Based on the above findings, it is reasonable to hypothesize that the Neu5Gc-carrying serum glycoproteins enter the cell via fluid phase pinocytosis, eventually reaching the lysosome, where they are exposed to the lysosomal sialidase. The resulting free Neu5Gc in the lysosome would then have the opportunity to use the lysosomal sialic acid transporter to reach the cytosol in order to be salvaged and eventually converted to CMP-Neu5Gc.

To test this hypothesis, the GM05520 mutant human fibroblasts, which are completely deficient in the lysosomal sialic acid transporter, as well as GM01718 mutant human fibroblasts, which have less than 1% lysosomal sialidase activity compared to normal fibroblasts, were used. For these studies, it was important to differentiate between cell surface and internal Neu5Gc. Thus, instead of subcellular fractionation, the method of flow cytometry was utilized, using our previously described affinity purified Neu5Gc-specific chicken antibody. As shown in FIG. 7A, after 3 days of feeding with 10% FCS+20% horse serum (both rich sources of glycoprotein-bound Neu5Gc), the total surface expression of Neu5Gc was significantly lower in both mutant fibroblasts compared to WT fibroblasts. Permeabilization of cells revealed similar levels of total Neu5Gc glycoconjugates (FIG. 7A), but the majority in the two mutants was internal (FIG. 7B). To confirm trapping of Neu5Gc glycoconjugates in lysosomes, fluorescence microscopy analysis was performed of permeabilized fibroblasts, co-labelling cells with a known marker for lysosomes, LAMP-1. An even distribution of Neu5Gc staining on WT normal fibroblasts with little co-localization with lysosomes (FIG. 7C) was found. On the other hand, both the lysosomal sialidase and the transporter mutants demonstrated significant accumulation of Neu5Gc glycoconjugates in the lysosomes (FIG. 7C).

The results with the sialidase-deficient fibroblasts confirm our hypothesis that this enzyme must act to release free Neu5Gc from glycoproteins and to make it available for metabolic incorporation. The accumulation of Neu5Gc glycoconjugates in the lysosomal transporter mutant was unexpected. A likely explanation is that accumulation of free Sia at a high concentration in the lysosomes inhibits the action of the lysosomal sialidase, resulting in accumulation of glycosidically-bound Neu5Gc. The residual levels of Neu5Gc detected on the surface of both mutant cells might be explained by direct incorporation of gangliosides and GPI-anchored proteins bearing Neu5GC from the serum. Taken together these data indicate that bound Neu5Gc molecules that enter into human cells via pinocytosis are released by the lysosomal sialidase and are then transported by the lysosomal sialic acid transporter to the cytosol, where they are available for activation and incorporated into glycoconjugates (FIG. 8). Of course depending on the type of glycoprotein involved, bound Neu5Gc could also be delivered to lysosomes via other pathways of endocytosis, e.g., receptor-mediated endocytosis via clathrin-coated vesicles.

It has long been assumed that free sialic acids could not be efficiently incorporated into cells because of their negative charge and hydrophilic nature. Thus, neutral ManNAc has traditionally been used as a precursor to feed cells, for conversion into Neu5Ac. The same concept has been applied to various unnatural mannosamine derivatives, and the addition of O-acetyl esters to the hydroxyl groups of mannosamine derivatives has been used to enhance delivery across the plasma membrane. In fact, one early study suggested that radioactive sialic acids could be incorporated into cells, and more recent work of others has shown "efficient" uptake of a variety of kinds of sialic acids into cells. However, the kinetics of incorporation showed no evidence of saturation even at >10 mM concentrations, suggesting that the uptake was not due to a high efficiency cell surface transporter for sialic acids. The work using a natural sialic acid (Neu5Gc) gave similar results.

The present study resolves all these discrepancies by showing that free sialic acids from the medium can be taken up into cells via non-clathrin-mediated mechanisms, mostly amiloride-sensitive fluid-phase pinocytosis. The content of the resulting pinocytotic vesicles and endosomes would eventually be delivered to the lysosome, where the previously described sialic acid transporter then delivers the molecules into the cytosol. We also show that the incorporation of glycosidically-bound Neu5Gc from exogenous glycoproteins occurs by similar delivery to the lysosome, and release by the lysosomal sialidase, followed by export into the cytosol (FIGS. 7 and 8). Once activated to CMP-Neu5Gc, molecules from both sources (free and originally bound) would be indistinguishable from those that were endogenously synthesized by the cells.

Most recently, it has been shown that human embryonic stem cells can incorporate Neu5Gc from medium glycoconjugates, making them targets for the naturally occurring antibodies that circulate in most humans. Preliminary data also suggest that these antibodies could also be related to diseases in intact humans. Thus, the mechanism by which Neu5Gc is incorporated into human cells is of potentially great importance. Further studies of this process are also relevant both to the ongoing attempts by various groups to incorporate different kinds of unnatural sialic acids into cultured cells, and also to our efforts to understand how exogenous dietary Neu5Gc gain entry into normal human tissues. In this regard, it is of note that Neu5Gc accumulation appears to be enhanced in naturally occurring tumors, and in fetal tissues. It is suggested that this may be explained by the fact that fluid-phase macropinocytosis is enhanced by growth factors, which are expected to be very prominent in these two situations.

Finally, it is believed that this is the first reported example in which an extracellular small molecule that cannot cross the plasma membrane is delivered efficiently to the cytosol utilizing fluid pinocytosis and a specific lysosomal transporter. The approach could thus potentially be generalized to any small molecule that has a specific lysosomal transporter, but not a plasma membrane transporter. For example, one could envisage that the neutral sugars GlcNAc and GalNAc, which do not have a high efficiency plasma membrane transporter could nevertheless be delivered to the cytosol via the lysosomal GlcNAc/GalNAc transporter. The prediction is that adding millimolar concentrations of these sugars into the medium would result in significant delivery to the cytosol.

Example 2

The H1 ES cell line (WiCell Research Institute, Inc., Madison, Wis.) cells were cultured on mitotically inactivated (mitomycin C treated) mouse embryonic fibroblasts (MEF, Specialty media, Phillipsburg, N.J.) in DMEM/F12 Glutamax (Gibco, Carlsbad, Calif.), 20% "KNOCKOUT" serum replacement (Gibco) or pooled human blood-type AB serum (Pel-Freeze, Rogers, Ariz.), 0.1 mM non-essential aminoacids (Gibco), 0.1 mM beta-mercaptoethanol (Gibco), and 4 ng/mL BFGF-2 (R&D systems, Minneapolis, Minn.). For EB culture, H1 ES cells were grown in suspension for 7-10 days, using the same medium without FGF-2 and 10% serum. Cells were changed to a new dish every day to eliminate eventual fibroblast contamination.

HESC Transfection. H1 HESC were stably transfected to express green fluorescent protein (GFP) by CAG-EGFP SIN lentivirus infection. The SIN lentiviral vector expressing EGFP under control of the CAG promoter was derived from a multiply attenuated HIV vector system, but included a U3 deletion and introduction of a cPPT element. Vectors were produced by triple transfection of 293 cells followed by ultracentrifugation and titration as previously described[30]. Undifferentiated cells were exposed to the virus at a titer of 0.5× $10^{10}$ gtu/mL for 1 hour followed by a 2 day recovery period. EGFP was detected by native fluorescence at day 3 after transduction. Cells expressing EGFP were FACS sorted for uniform EGFP expression. No loss in EGFP expression was observed during propagation or EB differentiation and up to 10 months after transduction. The EGFP positive cells derived from these colonies are thus polyclonal in origin. The GFP positive ES cells maintain a similar phenotype to the wild type cells (SSEA-4, SSEA-3 and Oct4-positive).

Oct-4 antibody (1:500) was from Santa Cruz (Santa Cruz, Calif.), the other marker antibodies (SSEA-3, TRA-1-60, alkaline phosphatase and nestin) were from Chemicon (Temecula, Calif.; dilution 1:100), and the secondary Cy3 antibody from Sigma (San Louis, Mo.; dilution 1:250). Alkaline Phosphatase (AP) activity was measured using the Vector Red Alkaline Phosphatase substrate kit I from Vector laboratories (Burlingame, Calif.).

Human Sera—

Sera from several healthy human donors were obtained after written consent and Institutional Review Board approval, and anonymously numbered before further use. Anti-Neu5Gc antibody levels in several serum samples were determined as described elsewhere[13]. Two specific sera, corresponding to the lowest and highest extremes of the range, were selected for the experiments. Another serum with a high level of anti-Neu5Gc antibodies was also tried with identical results to those presented in the figures.

Determination of Neu5Gc Content—

Sias from HESC, feeder layer cells, EB or culture medium were released by mild acid, derivatized with 1,2-diamino-4,5-methylene dioxybenzene (DMB) and analyzed by HPLC to determine the percentage of Neu5Gc in total Sias[13].

Flow Cytometry—

Cells were harvested into 2 mM EDTA in phosphate buffer (PBS) and washed with PBS. $1 \times 10^5$ cells were incubated with a chicken anti-Neu5Gc (1.5 µg/100 µL) and stained with a donkey anti-chicken IgY conjugated to Cy5 (Jackson, West Grove, Pa.; dilution 1:100 in PBS). Neu5Gc-specific antibody binding was partially blocked by co-incubation with 1% chimpanzee serum, which (unlike human serum) is rich in Neu5Gc.

For human serum antibody deposition studies, HESC were harvested and exposed to individual human sera. Human IgGs deposited on the cells were stained with an anti-human IgG conjugated to Alexa 594 (Molecular Probes, Carlsbad, Calif.; dilution 1:100 in PBS). For C3b deposition, HESC were exposed to human serum, then incubated with a goat anti-human C3b (Fitzgerald, Concord, Mass.; dilution 1:100 in PBS) and finally stained with an anti-goat IgG conjugated to Alexa 594 as above.

Cytotoxicity Assays—

A standard procedure for testing antibody:complement-mediated cytotoxicity after exposure to human sera was followed. HESC were harvested as described and resuspended into $GVB^{2+}$ buffer (Sigma) alone (control) or $GBV^{2+}$ containing 25% human serum. Cells were incubated for 2 h at 37° C. and gently shaken. Dead cells were stained with propidium iodide (5 µg/mL) and analyzed by FACS. For cytotoxicity assays on the plate, cells were exposed to serum-free HESC culture medium containing 25% of the test human sera. After 30 minutes at 37° C., they were harvested and stained with propidium iodide.

Statistical Analysis—

Sia content from at least two experiments run in duplicate was analyzed using the T test in Microsoft Excel. Data are expressed as mean±standard deviation.

Presence of Neu5Gc on HESC Grown Under Standard Conditions

Neu5Gc on HESC was detected using an affinity-purified chicken polyclonal monospecific anti-Neu5Gc antibody[13]. HESC stably expressing EGFP were gated for EGFP-positivity to separate them from contaminating feeder layer fibroblasts. The antibody stained HESC growing in standard conditions, and binding was partially blocked by Neu5Gc-containing glycoproteins from chimp serum (FIG. 9a). Blocking was incomplete, likely because not all possible epitopes recognized by the polyclonal antibody are present in chimpanzee serum[13].

To chemically analyze the Sia content of HESC, we separated them from the feeder layer fibroblasts by FACS sorting using their EGFP signal. Feeder-layer-free EB derived from HESC were also examined without sorting. Both the membrane and cytosolic fractions from HESC and EB had a peak corresponding to Neu5Gc (FIG. 9b), whose identity was confirmed by electrospray mass spectrometry (data not shown)[13]. HESC membranes contained 17.88±1.47 pmoles Sia/pig protein with 9.31±3.70 pmoles Sia/µg protein in the cytosolic fraction. The percentage of total Sias present as Neu5Gc varied from 6-10.5% in the membranes and from 2.5-9% in the cytosolic fraction. EB membranes had 16.59±13.88 pmoles Sia/µg protein with 9.13±0.10 pmoles Sia/ng protein in the cytosolic fraction. The percentage of total Sias present as Neu5Gc in EB varied from 5-17% for the membranes and 6.5-11% for the cytosolic fraction.

Identifying Potential Sources of Neu5Gc in HESC

Since human cells are unable to synthesize Neu5Gc[12], the Neu5Gc detected likely originated from elsewhere, eventually being metabolically incorporated by the HESC. As expected for other mammals, Neu5Gc represented 20% of total Sias in the mouse feeder layer (0.91±0.13 nmoles/million cells). However, uptake from feeder cells cannot explain all the Neu5Gc found in HESC, since removal of the layer to obtain EB did not eliminate it. Our ongoing studies have shown that human cells can take up Neu5Gc from the medium and metabolically incorporate it into membrane glycoconjugates. The "serum replacement"-containing medium used to support HESC growth was found to contain 35.93 nmoles Neu5Gc/mL, representing 54% of total Sias. The commercial "KNOCKOUT" "serum replacement", used for preparing this medium is the major source of Neu5Gc, since it contains 129 nmoles/mL. In contrast, medium without any additives is poor in Neu5Gc (0.008 nmoles/mL).

Neu5Gc Content of HESC is Reduced by Growth in Heat-Inactivated Human Serum with Low Anti-Neu5Gc Antibodies Culture in heat-inactivated pooled normal human serum could markedly reduce Neu5Gc in human colon carcinoma cells[13], apparently due to metabolic replacement by Neu5Ac in the human serum. HESC was therefore incubated in medium containing heat-inactivated human serum instead of the standard serum replacement (an approach already suggested by others for different reasons)[14, 15]. First, a lot of pooled human serum was screened and defined in which natural anti-Neu5Gc antibodies were very low (hereafter called NHS). In case any residual antibodies were active, heat inactivation was used to eliminate complement. HESC incubated in such NHS remained undifferentiated on the feeder layer, expressing typical levels of markers of non-differentiation (alkaline phosphatase, Oct-4, SSEA-3, SSEA-4, TRA-1-60, and TRA-1-81; see examples in FIG. 10a), and lack of all differentiation markers tested (FIG. 10a). After feeder layer removal, these HESC were able to develop into normal EB.

Neu5Gc incorporation into HESC membranes dropped after 3 days (from ~4 pmoles/µg protein to 0.34±0.06 pmoles/µg protein) and down to 0.13±0.01 moles/µg protein after one week (~1% of total Sia as Neu5Gc, see FIG. 11). The required presence of the mouse feeder layer apparently prevented complete elimination of Neu5Gc from HESC. After growing for 3 days in human serum, some HESC were differentiated into EB either in 10% commercial serum-replacement, or in 10% NHS, without a feeder layer. After one week in serum-replacement, the amount of Neu5Gc on the EB membranes increased (from 0.34±0.06 to 0.40±0.10 pmoles/ng protein). In contrast, continued incubation in NHS further reduced Neu5Gc levels to 0.047±0.06 pmoles/µg protein.

Natural Human Anti-Neu5Gc Antibodies Bind to HESC and Cause Complement Deposition.

Healthy humans have variable levels of "natural" circulating anti-Neu5Gc antibodies[13]. We asked whether such antibodies could recognize Neu5Gc-containing epitopes on HESC grown under standard conditions. Cells exposed to a high-level anti-Neu5Gc antibody-containing human serum (Hi-GcAbHS) showed human IgG binding (FIG. 12a shows only the EGFP+HESC). In contrast, staining of cells exposed to a low-level anti-Neu5Gc antibody-containing human serum (Lo-GcAbHS) was almost similar to that of non-exposed controls. Antibody deposition was related to the amount of Neu5Gc on the HESC, since cells growing in NHS did not show any IgG binding when exposed to the same Hi-GcAbHS (FIG. 12b).

Cell surface antibody deposition can activate the classical complement pathway, eventually leading to killing or phagocytosis. We asked if complement C3b deposition occurred following exposure to Hi-GcAbHS. As before, we show the data gated for EGFP+HESC. When HESC were grown under the standard conditions, 37% were positive for C3b (FIG. 13c; compare to 0% background in FIG. 13a). Only 22% of the cells were positive after exposure to Lo-GcAbHS, with actual levels on individual cells being much lower (FIG. 13b, note that the Y-axis is a log scale), When HESC were grown for 5 days in NHS-containing medium, C3b-positivity after exposure to Hi-GcAbHS dropped to 13% (FIG. 13c). These data are consistent with deposition of anti-human IgG under the same conditions (FIG. 12) and also with the significant reduction in Neu5Gc on the HESC after incubation in human serum-containing medium (FIG. 11).

Such binding of antibody and complement to HESC would target them for death in vivo, via recognition by macrophages and NK cells. Regardless, attempts were made to directly determine antibody: complement-mediated cytolysis on HESC in vitro. The standard single cell suspension required for such analyses caused extensive cell death even under control conditions (without serum). Exposure to Hi-GcAbHS caused increased death above background levels seen with NHS, from 40% to 60-70%. In contrast, the percentage of dead HESC after exposure to Lo-GcAbHS was similar to that of the control. When the assay was performed directly on the culture dish for shorter time, more HESC remained alive. Cell death with Hi-GcAbHS was higher than that of the control (14% vs. 10%), whereas the death rate after exposure to Lo-GcAbHS remained unchanged.

HESC and EB can incorporate the non-human Sia Neu5Gc from the murine feeder layer and/or the medium, leading to an immune response mediated by "natural" anti-Neu5Gc antibodies present in most humans. In effect, HESC appear like animal cells to the human immune system. Pooled, heat-inactivated human serum selected for low titers of anti-Neu5Gc antibodies could be substituted for the traditional animal serum or serum replacement, supporting the undifferentiated growth of HESC. This approach markedly reduced the immune response, by reducing the Neu5Gc content on the HESC.

Most existing HESC lines (including all those that are currently approved for study under federal funding in the US) have been grown or derived with mouse feeder layer[10]. Standard culture conditions also include animal serum, or a serum replacement. It is shown here that the commercial "serum replacement" is also a rich source of Neu5Gc, and both HESC and EB are able to incorporate it. While the composition of this serum replacement is under an international patent (WO 98/30679), the formulation includes proteins like transferrin, which are likely to be from animal sources and therefore, would carry Neu5Gc. Human orthologs or recombinant proteins synthesized in bacteria could be used instead.

Many efforts have been recently made to eliminate these animal-derived components[16]. The use of a feeder-free system, such as Matrigel or other components of the extracellular matrices, have been explored[6,17,18]. However, feeder-free conditions seem to facilitate in vitro evolution of HESC, selecting for aneuploid cells[19]. Moreover, many of the medium and matrix components are still from animal sources and contamination with Neu5Gc can be expected.

Human feeders of different origins have also been tried[20-22]. Richards et al. first reported successful derivation and culture of some HESC lines in the complete absence of non-human components, using feeder layers from human tissues with human serum and supplements, further demonstrating the ability to develop teratomas, i.e., confirming the maintenance of pluripotentiality. It was also noted that human serum did not cause any change in the undifferentiated state of the HESC. Others have also tried similar xeno-free techniques on hematopoietic stem cells by growing them on human stromal cells and using medium containing human AB serum. Of course, the use of an "all-human" environment carries a different set of risks (unexpected contamination with novel or newly emerging pathogens).

There are also potential implications for the incorporation of Neu5Gc with regard to general HESC biology. Many characteristic markers of HESC (SSEA-3, SSEA-4, TRA-1-60, and TRA-1-81) are glycolipids or glycoproteins, many of which can carry Sias. SSEA-4, which is highly expressed even in long-term cultures of HESC, is the sialylated form of the globo-series glycolipid SSEA-3 (Gb5) TRA-1-60 is a sialylated keratan sulfate protein and the TRA-1-81 epitope became accessible only after sialidase treatment. Neural lineage cells derived from EB express the polysialylated form of NCAM, as well as the antigen A2B5[26], which corresponds to polysialylated gangliosides. Since Sias are involved in self-recognition events, the presence of Neu5Gc instead of Neu5Ac could lead to unexpected impairments of cell function and tissue development.

Another possible solution is growth in heat-inactivated serum from the actual patient who is going to receive the therapy. Similar alternatives have been suggested for hematopoietic stem cells. Even if the patient serum contains anti-Neu5Gc antibodies, heat inactivation could prevent complement activation, until such time as the pre-existing Neu5Gc in the HESC is metabolically eliminated by the Neu5Ac in the serum. An added advantage to this approach is that it would screen for allogeneic cytotoxic antibodies in the recipient's serum.

The examples set forth above are provided to give those of ordinary skill in the art with a complete disclosure and description of how to make and use the preferred embodiments of the invention, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

Attached hereto are appendices A and B that are further meant to illustrate and not limit the invention.

We claim:
1. A cell line isolated from a viable and fertile transgenic mouse that
   a) comprises a genome having a homozygous mutation of the cytidine-5'-monophosphate N-acetyl neuraminic acid hydrolase (CMAH) gene,
   b) lacks expression of enzymatically active CMAH protein encoded by said CMAH gene, and c) lacks N-glycolylneuraminic acid (Neu5Gc) in one or more body fluid or tissue.

2. The cell line of claim 1, wherein the cell is selected from the group consisting of stem cells, epithelial cells and muscle cells.

* * * * *

UNITED STATES PATENT AND TRADEMARK OFFICE
CERTIFICATE OF CORRECTION

| | | |
|---|---|---|
| PATENT NO. | : 8,541,231 B2 | Page 1 of 1 |
| APPLICATION NO. | : 13/528507 | |
| DATED | : September 24, 2013 | |
| INVENTOR(S) | : Ajit Varki, Maria Hedlund and Dzung Nguyen | |

It is certified that error appears in the above-identified patent and that said Letters Patent is hereby corrected as shown below:

In the Specification

Column 1, line 17, under the "GOVERNMENT INTERESTS" section should read:

"This invention was made with government support under CA038701 awarded by the National Institutes of Health. The government has certain rights in the invention."

Signed and Sealed this
Fourth Day of March, 2014

Michelle K. Lee
*Deputy Director of the United States Patent and Trademark Office*